United States Patent [19]
Bodford et al.

[11] Patent Number: 5,928,209
[45] Date of Patent: Jul. 27, 1999

[54] BREATHABLE DISPOSABLE SANITARY PRODUCT CONSTRUCTION AND BACKSHEET THEREFOR

[75] Inventors: Carl Allen Bodford, Altanta, Ga.; Roe Clyde Allen, Crozet; Rahul Krishnakant Nayak, Stuarts Draft, both of Va.

[73] Assignee: Poly-Bond Inc., Waynesboro, Va.

[21] Appl. No.: 08/937,039

[22] Filed: Sep. 24, 1997

Related U.S. Application Data

[63] Continuation-in-part of application No. 08/720,631, Oct. 2, 1996, which is a continuation-in-part of application No. 08/552,727, Nov. 3, 1995, Pat. No. 5,643,239.

[51] Int. Cl.$^6$ .................................................... A61F 13/15
[52] U.S. Cl. ........................... 604/370; 604/367; 604/358
[58] Field of Search ..................................... 604/370, 367, 604/328, 322, 381, 358, 368

[56] References Cited

U.S. PATENT DOCUMENTS 5,643,239   7/1997   Bodford et al. .................. 604/370

*Primary Examiner*—Robert A. Clarke
*Attorney, Agent, or Firm*—Juettner Pyle Piontek & Underwood

[57] ABSTRACT

A breathable diaper, feminine hygiene, or like disposable sanitary product construction includes a plurality of materials including, from the skin-facing side outwardly, a topsheet of liquid- and vapor-permeable hydrophilic material. A core of highly absorbent material is disposed outwardly of the topsheet for absorbing fluid received through the topsheet, the core having an inner surface in fluid communication with the topsheet. A backsheet is disposed at least partially as an outer surface of the construction and is formed of a pouch defined by two layers of a non-woven hydrophobic and vapor-permeable material, with absorbent or superabsorbent particles therebetween, so that the backsheet limits the outward escape of liquid therethrough while enabling the outward escape of heat and water vapor therethrough. Each backsheet layer is an at least two-layer spunbound-meltblown SM or an at least three-layer spunbond-meltblown-spunbond SMS.

26 Claims, 21 Drawing Sheets

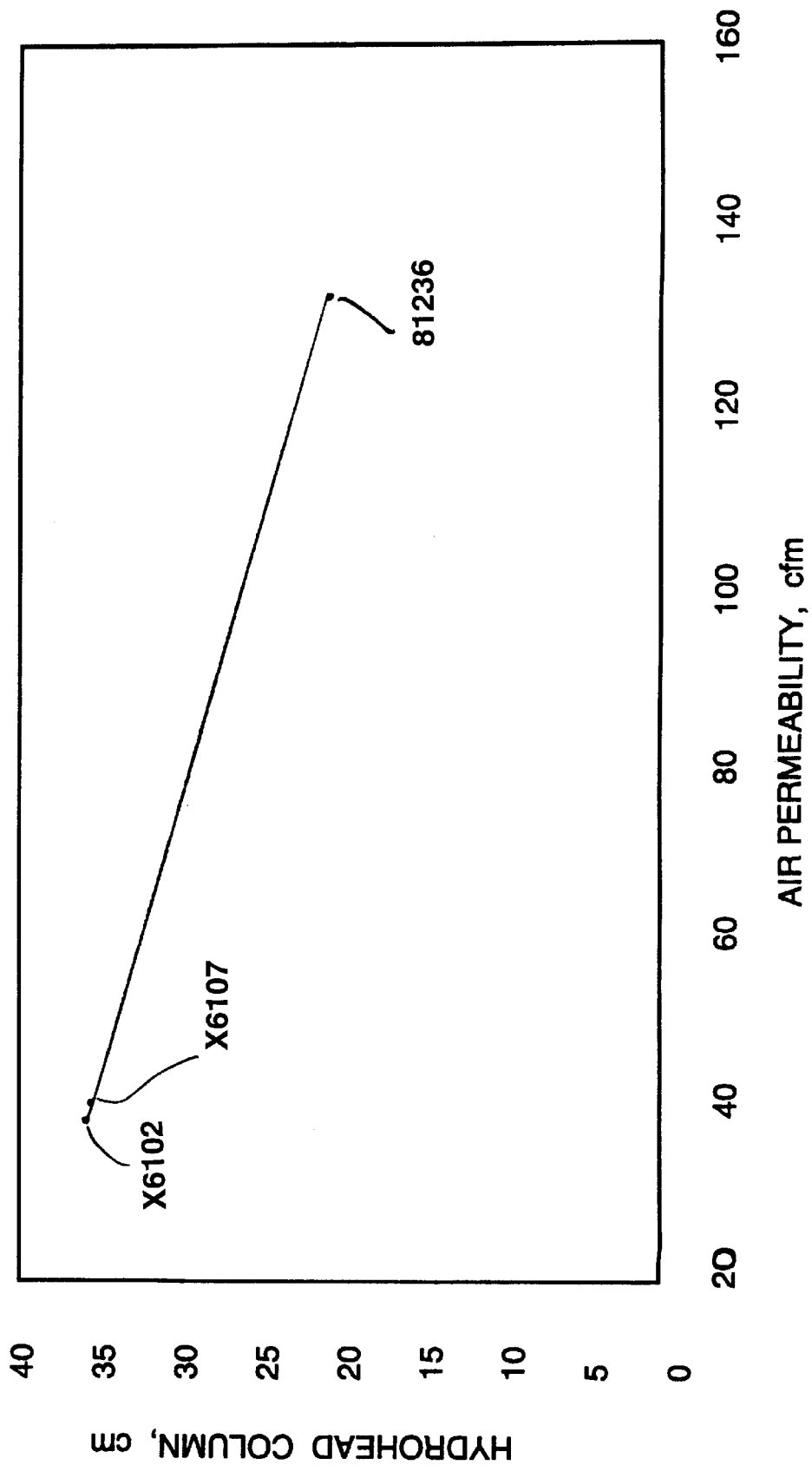

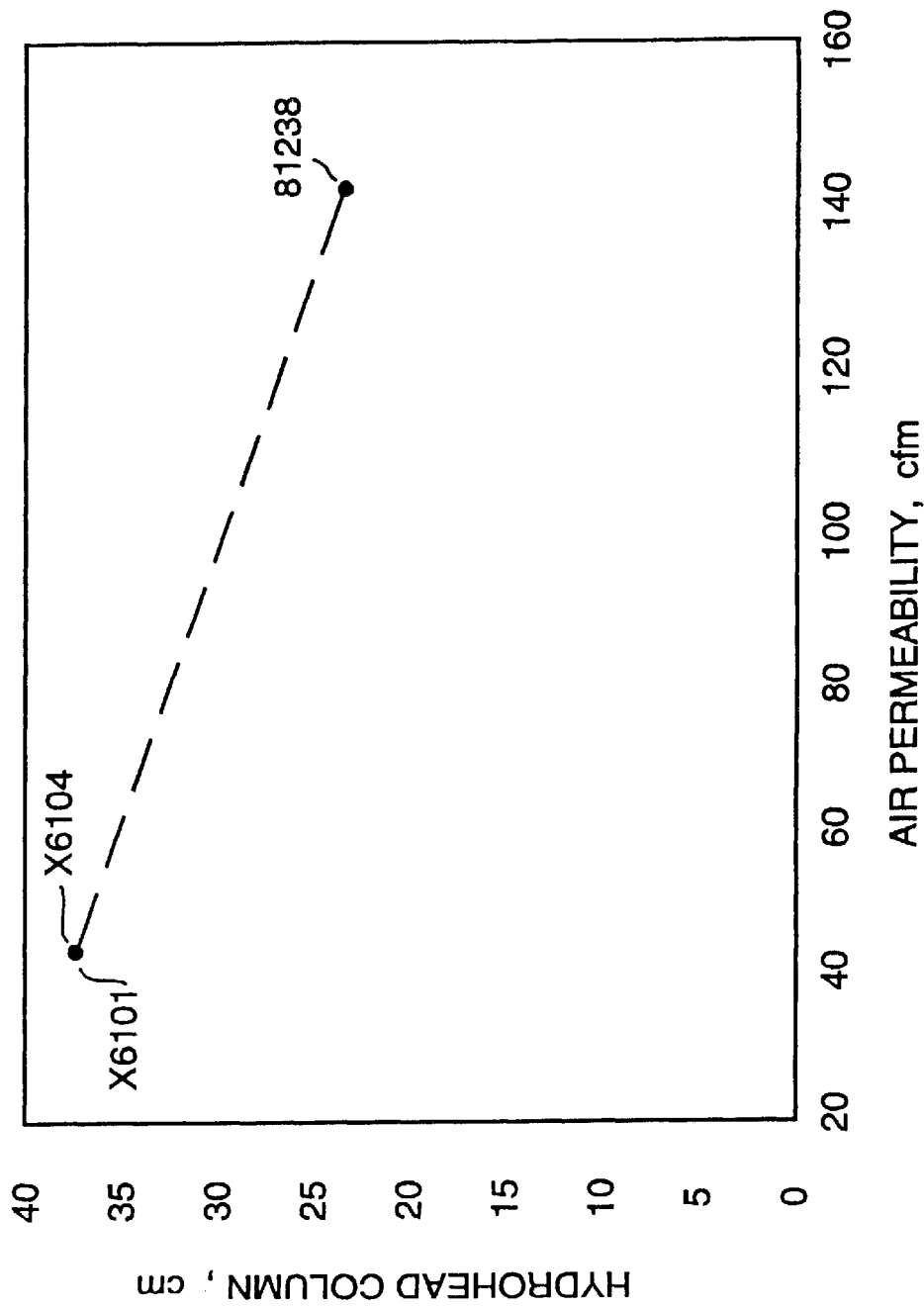

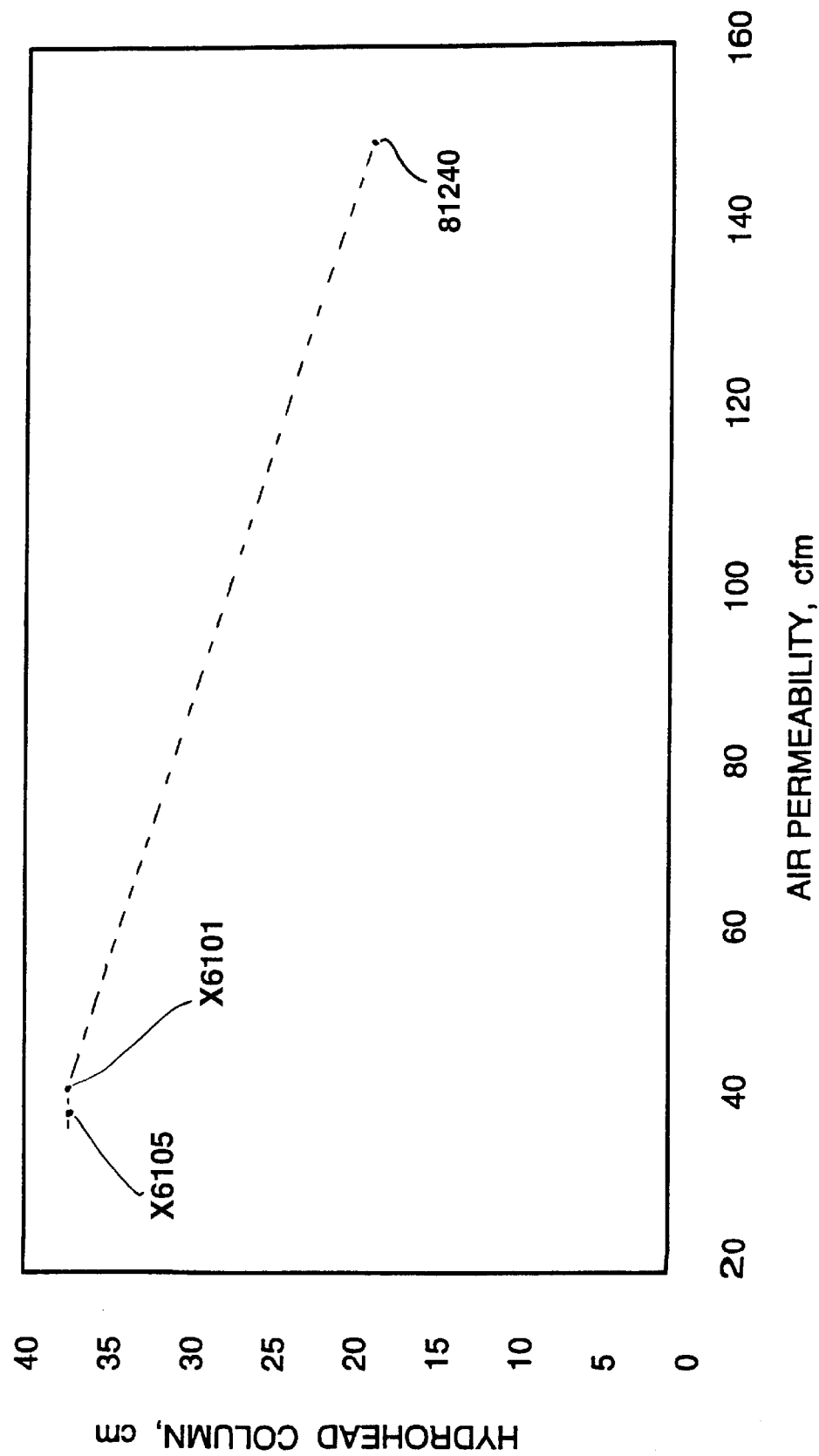
FIG. 14 HYDROHEAD COLUMN vs AIR PERMEABILITY

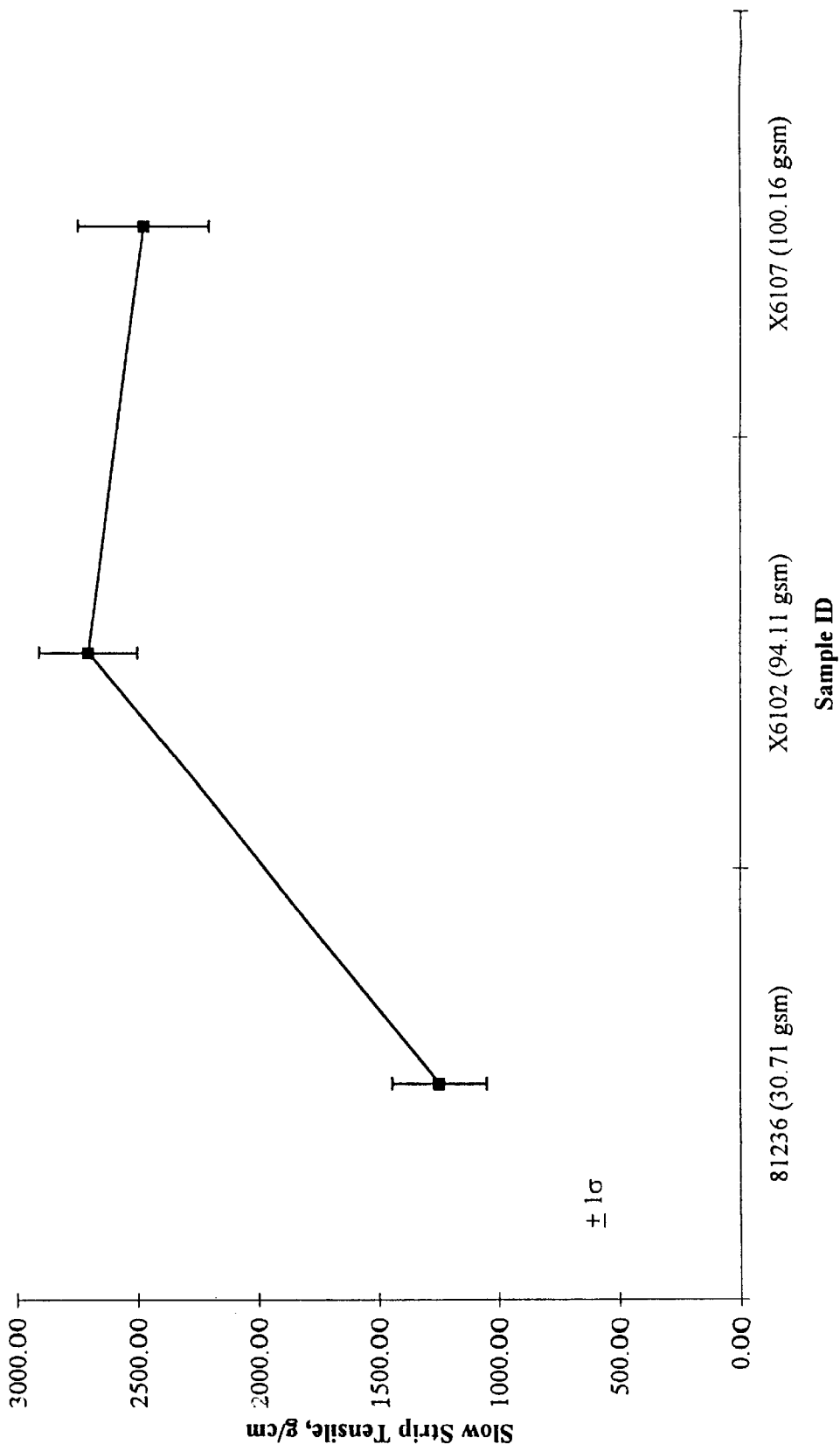
FIG. 15 Comparison of Base and Laminated 81236 Material Slow Strip Tensile Data in the Machine Direction

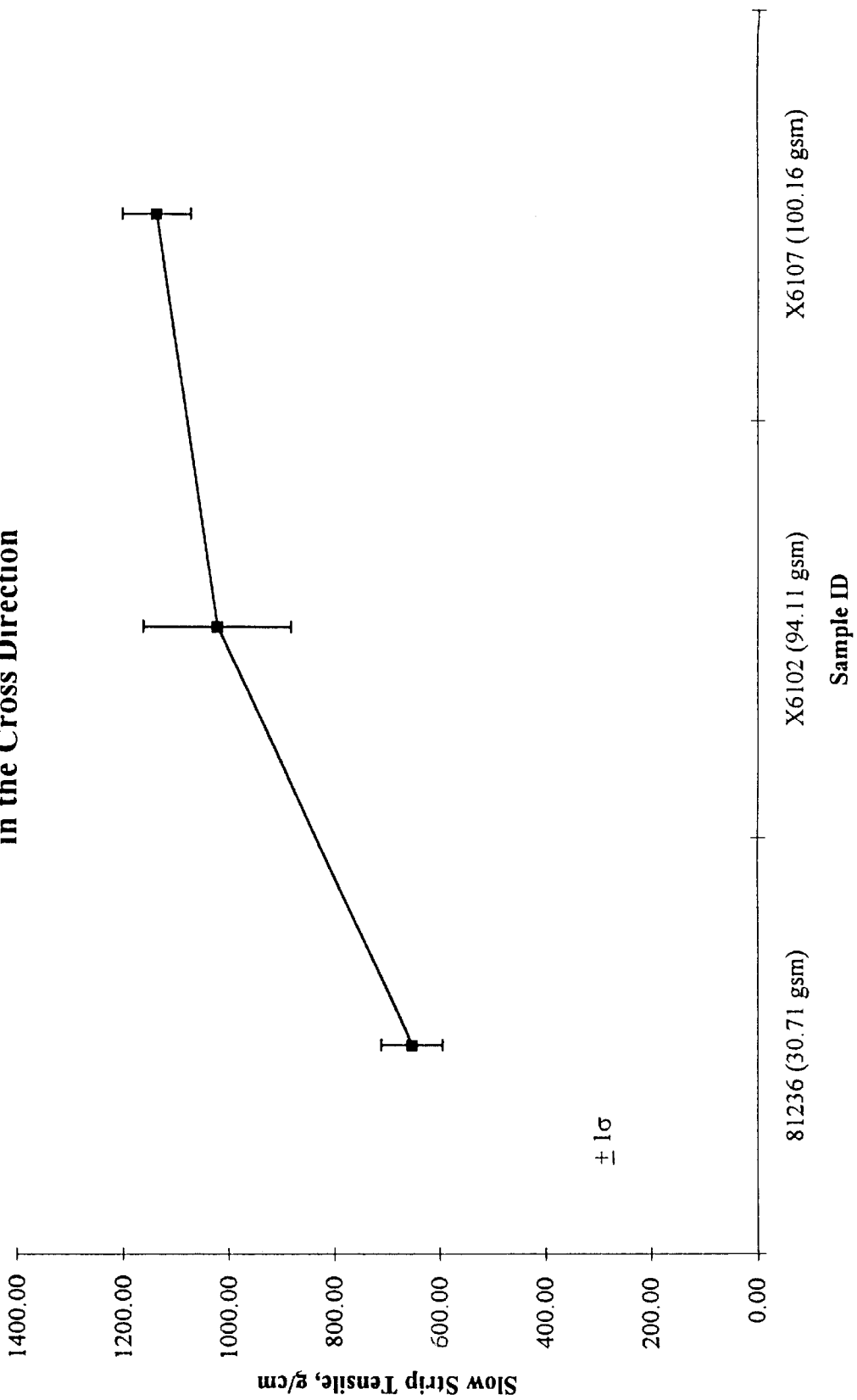

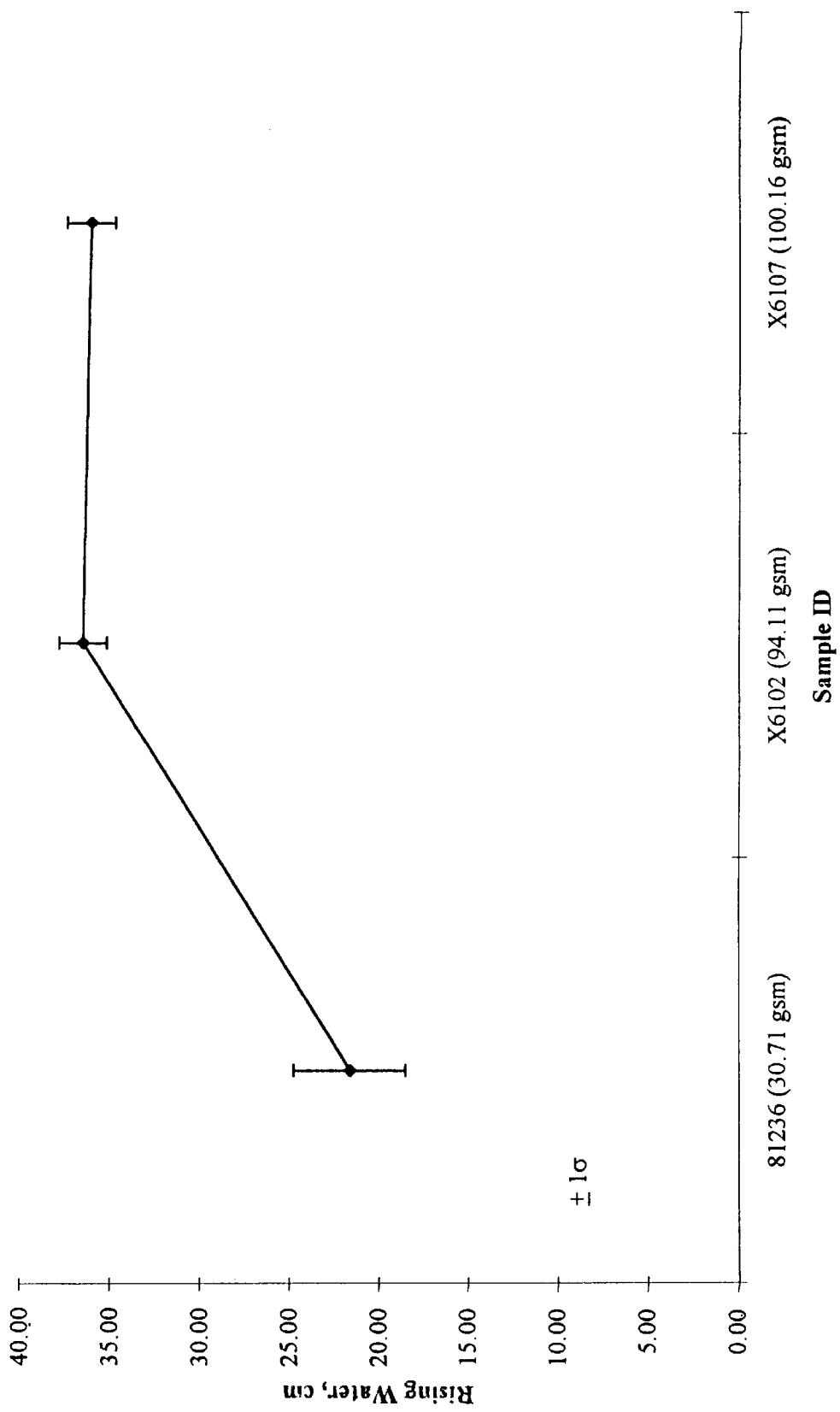
FIG. 17 Comparison of Base and Laminated 81236 Material Rising Water Data

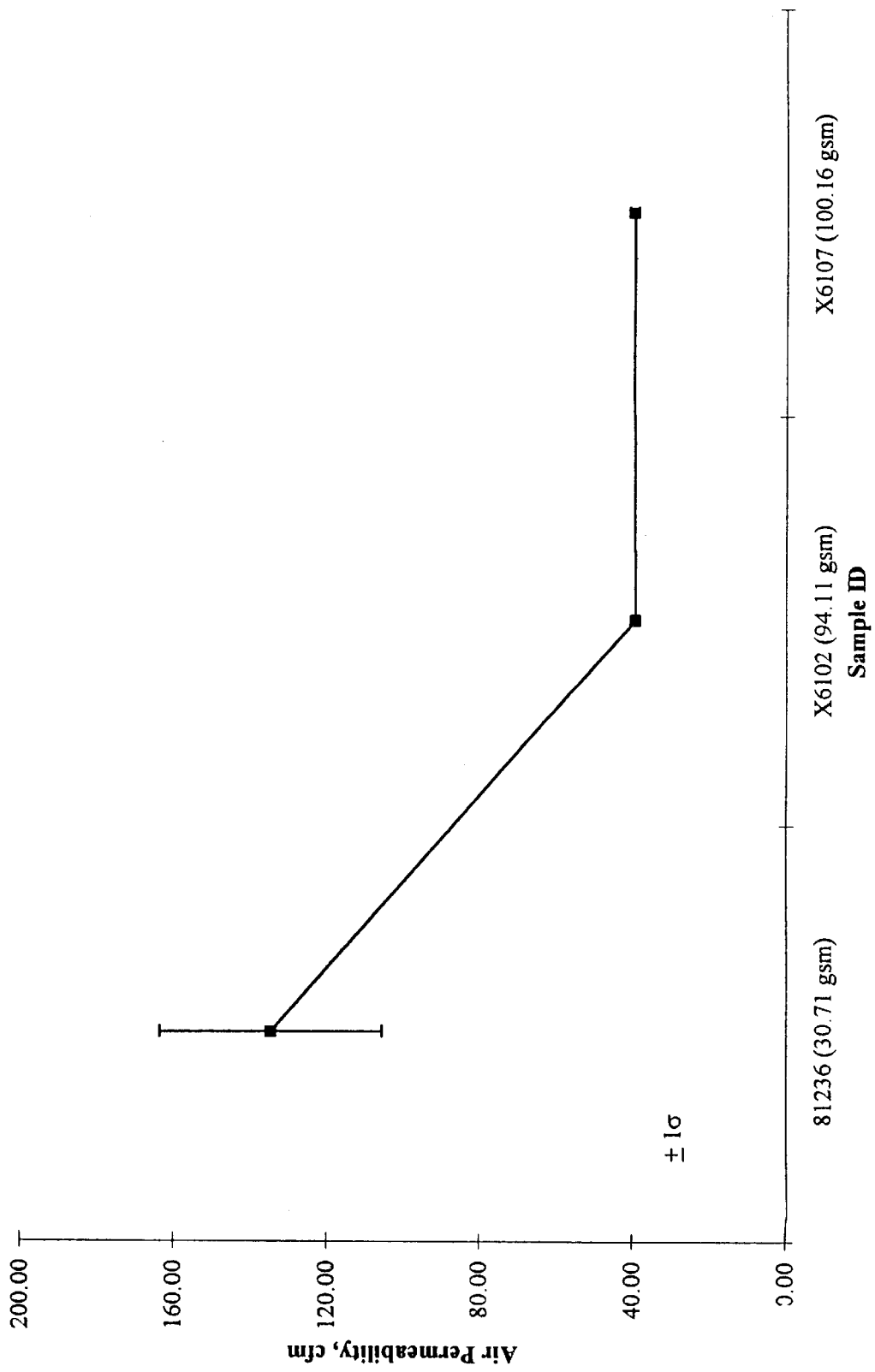

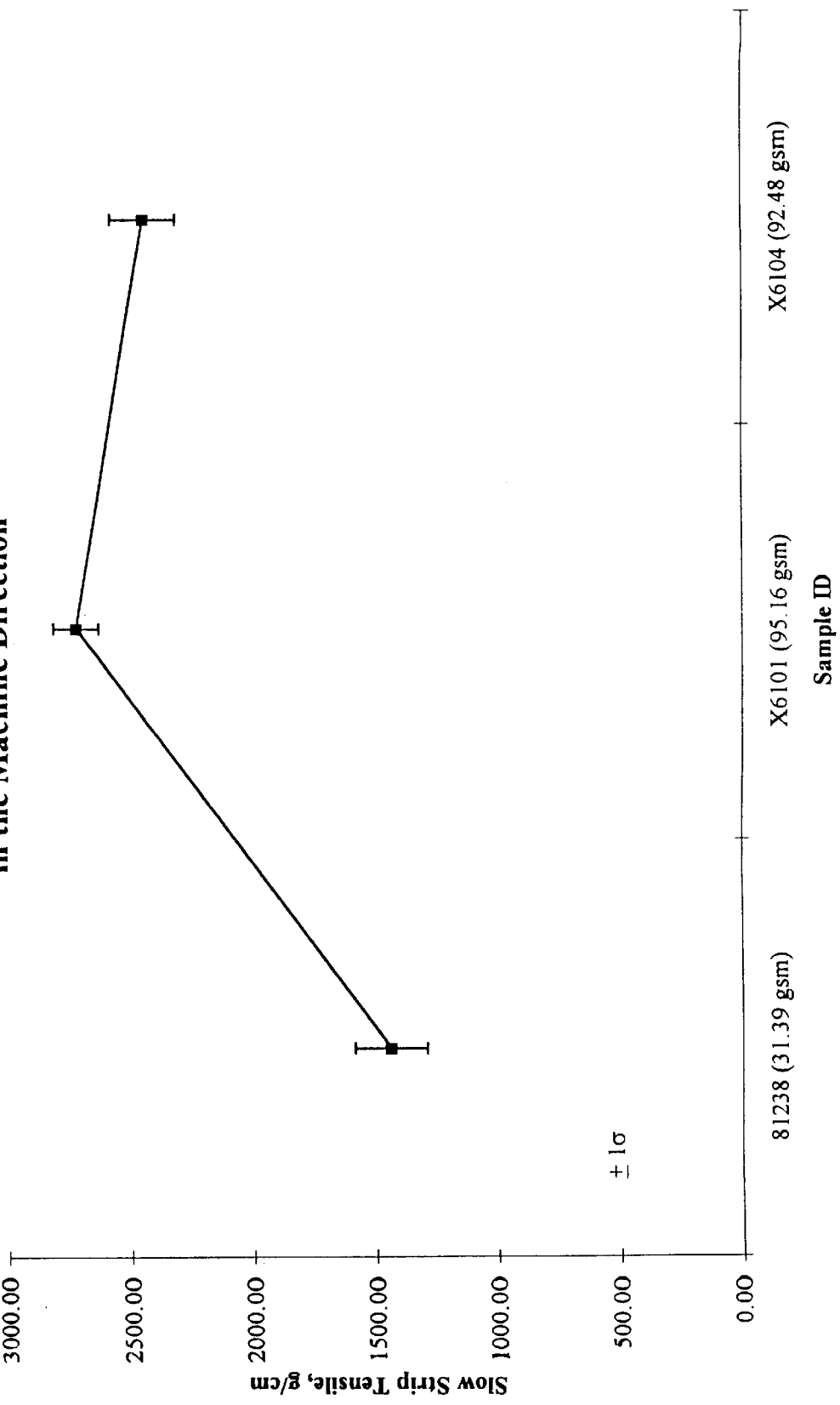
FIG. 19 Comparison of Base and Laminated 81238 Material Slow Strip Tensile Data in the Machine Direction

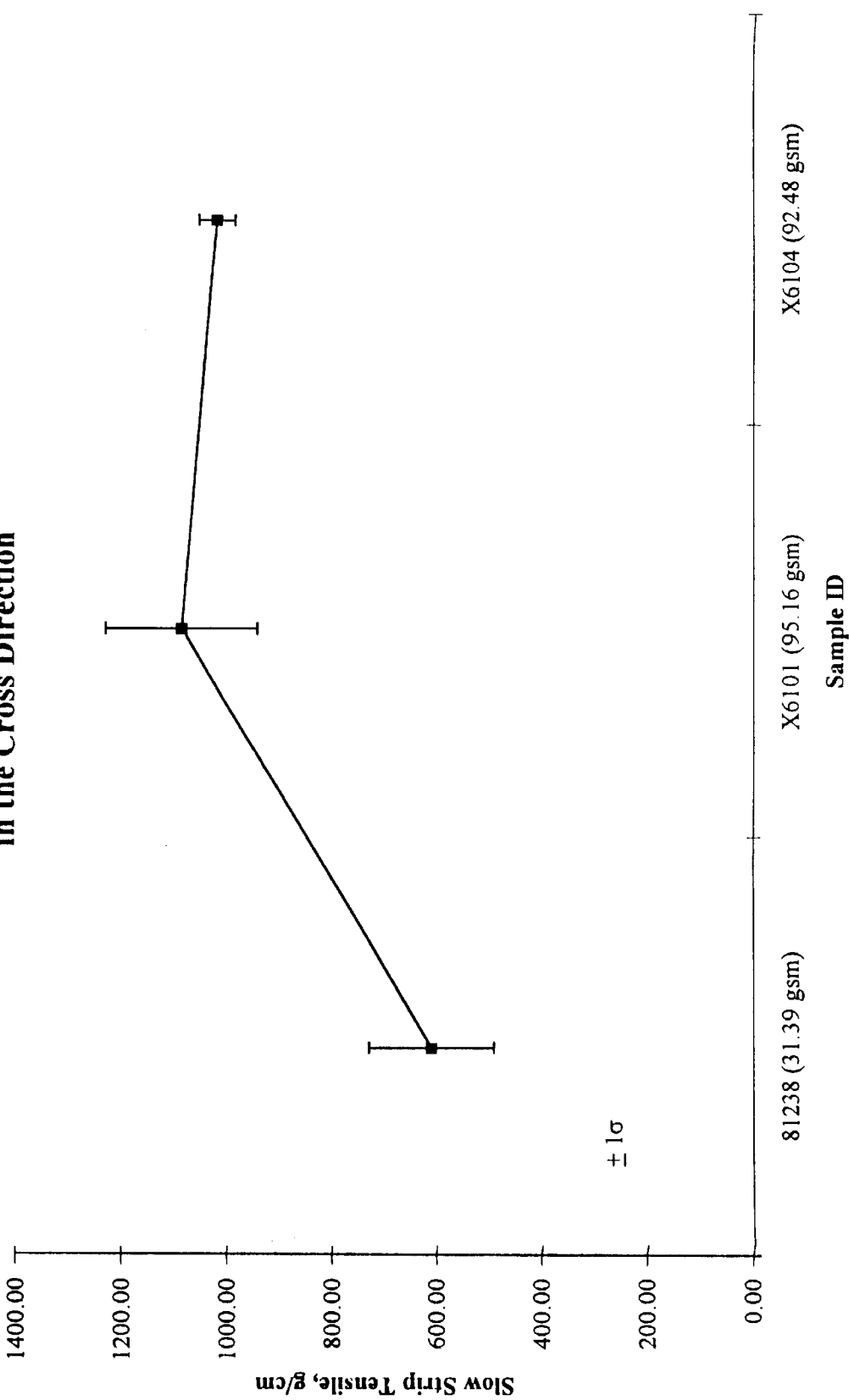
FIG. 20 Comparison of Base and Laminated 81238 Material Slow Strip Tensile Data in the Cross Direction

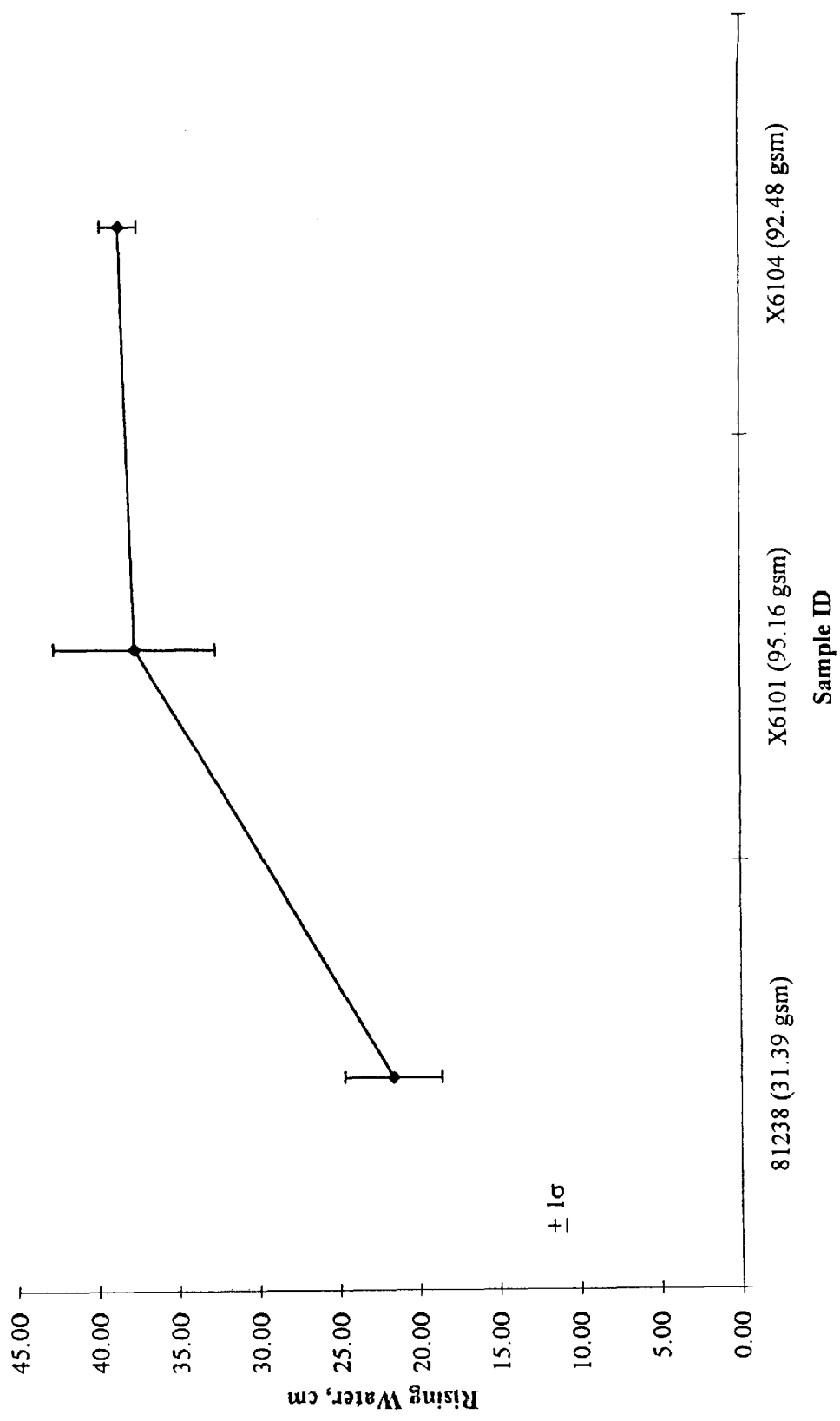
FIG. 21 Comparison of Base and Laminated 81238 Material Rising Water Data

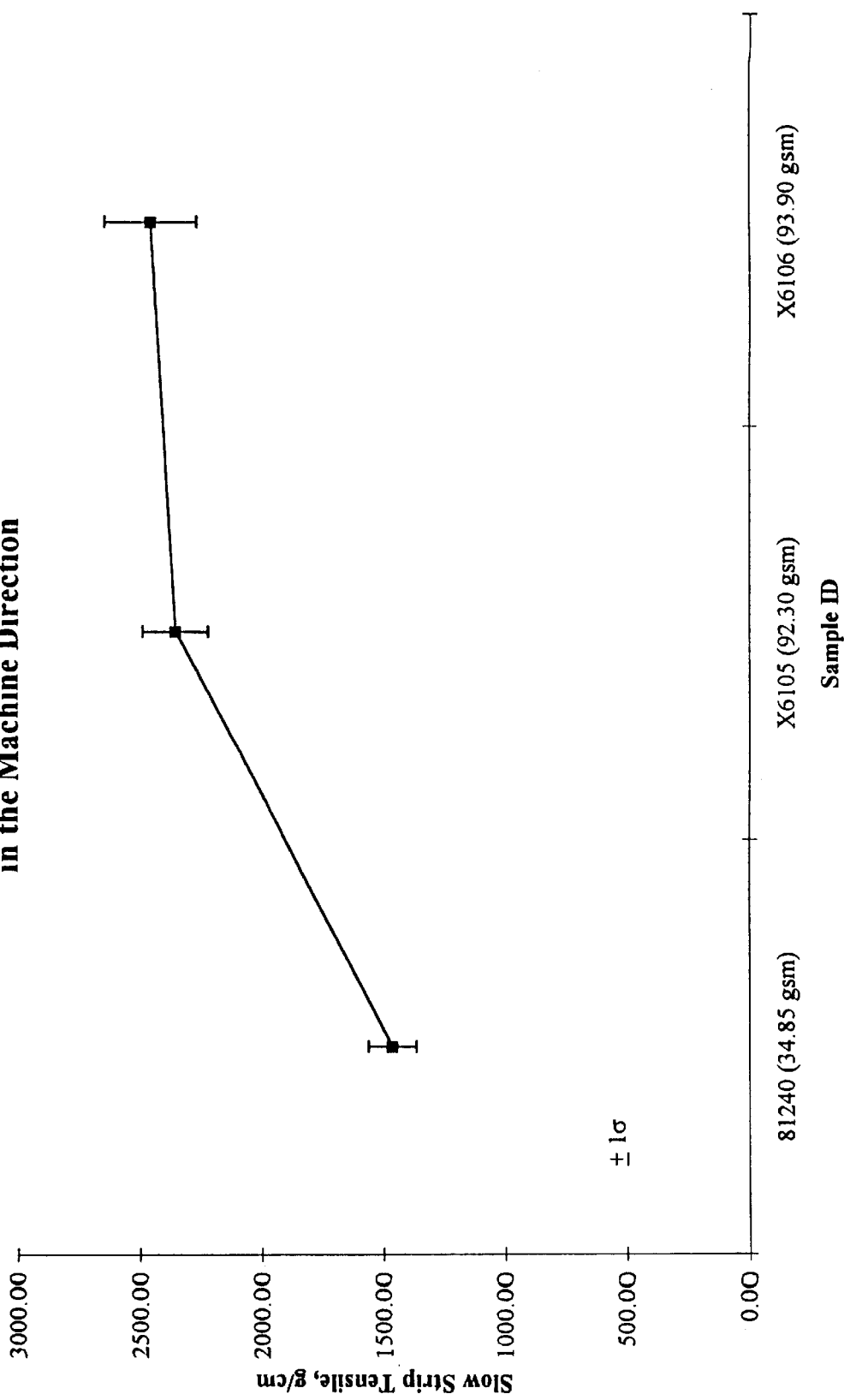
FIG. 23 Comparison of Base and Laminated 81240 Material Slow Strip Tensile Data in the Machine Direction

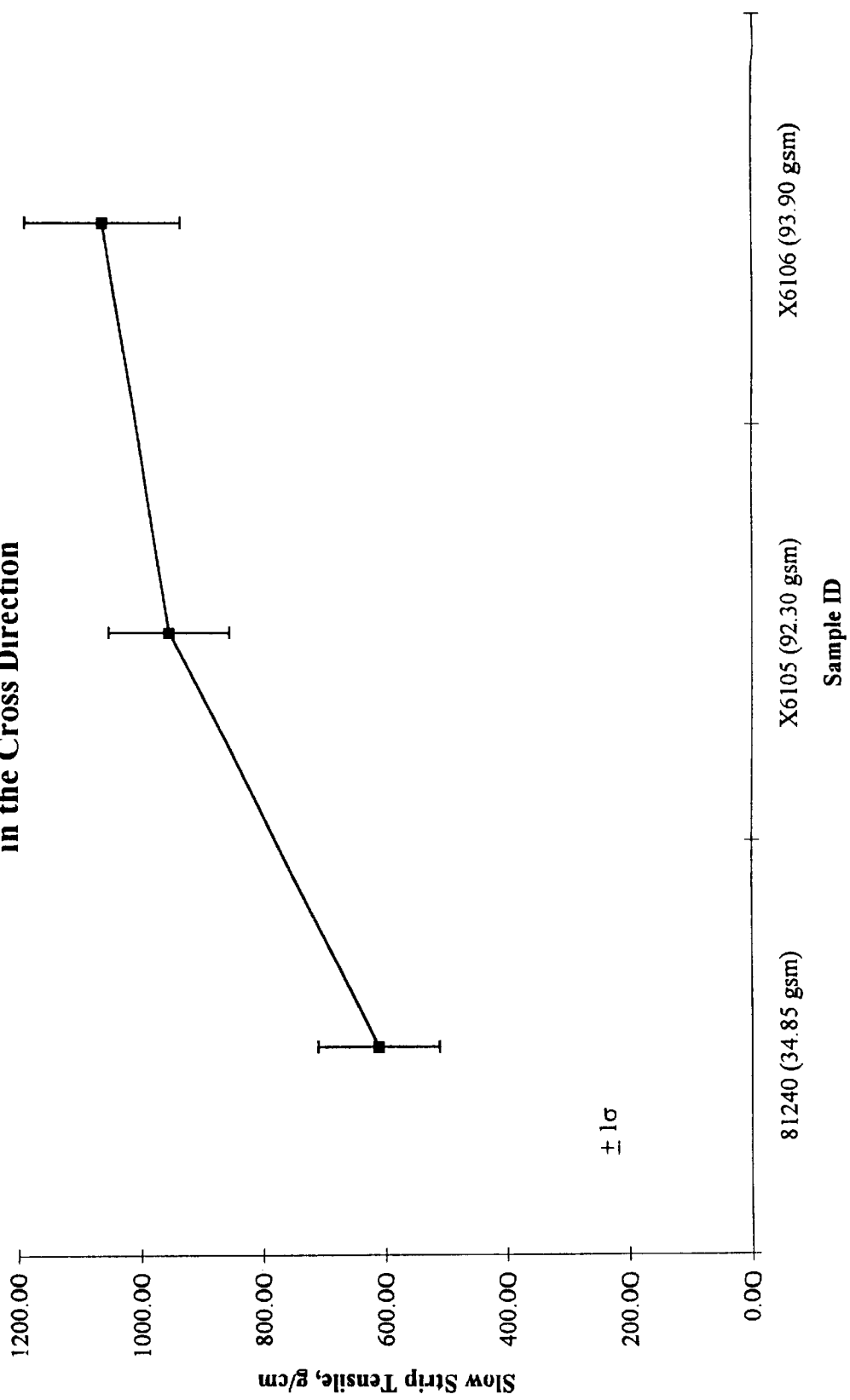

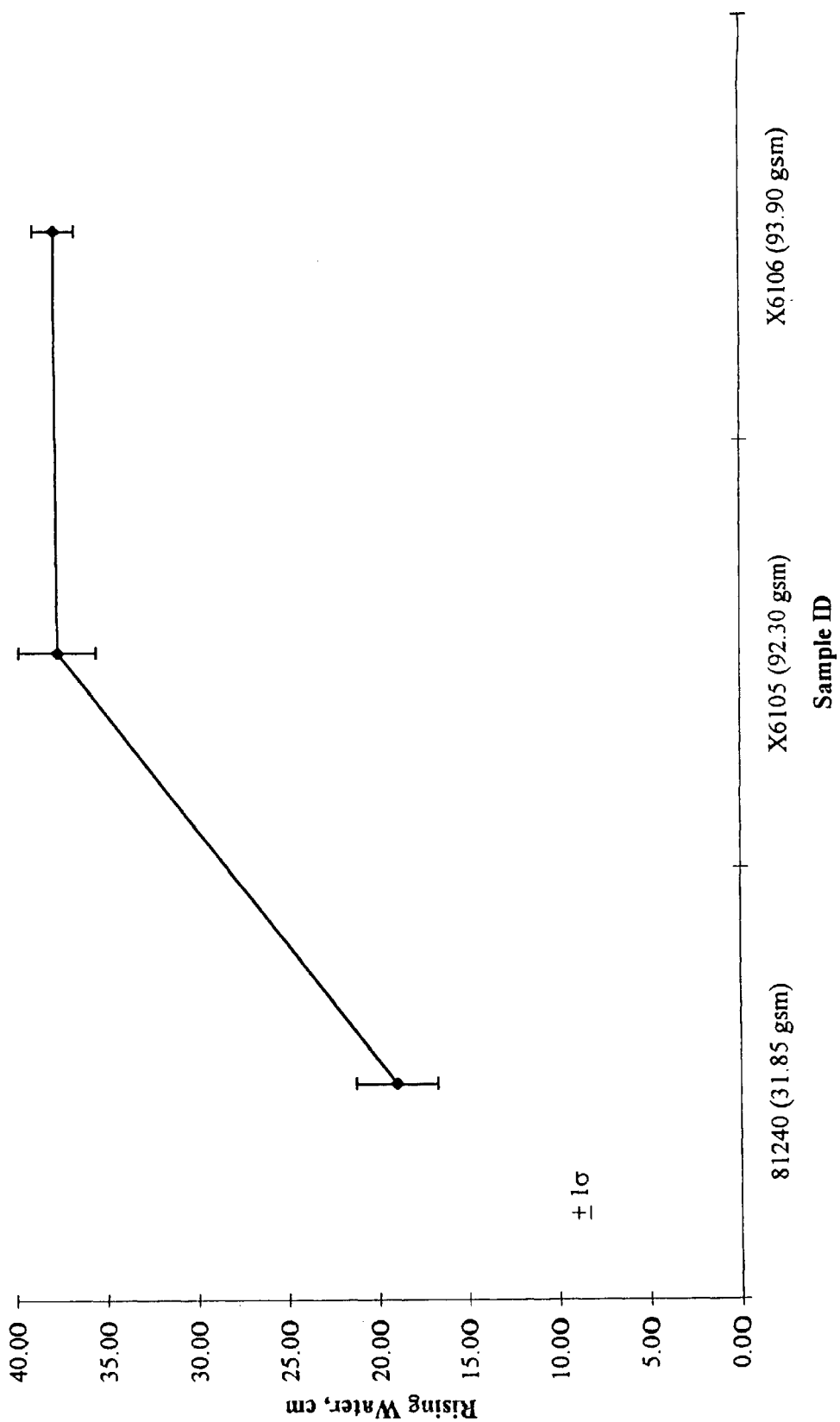
FIG. 25 Comparison of Base and Laminated 81240 Material Rising Water Data

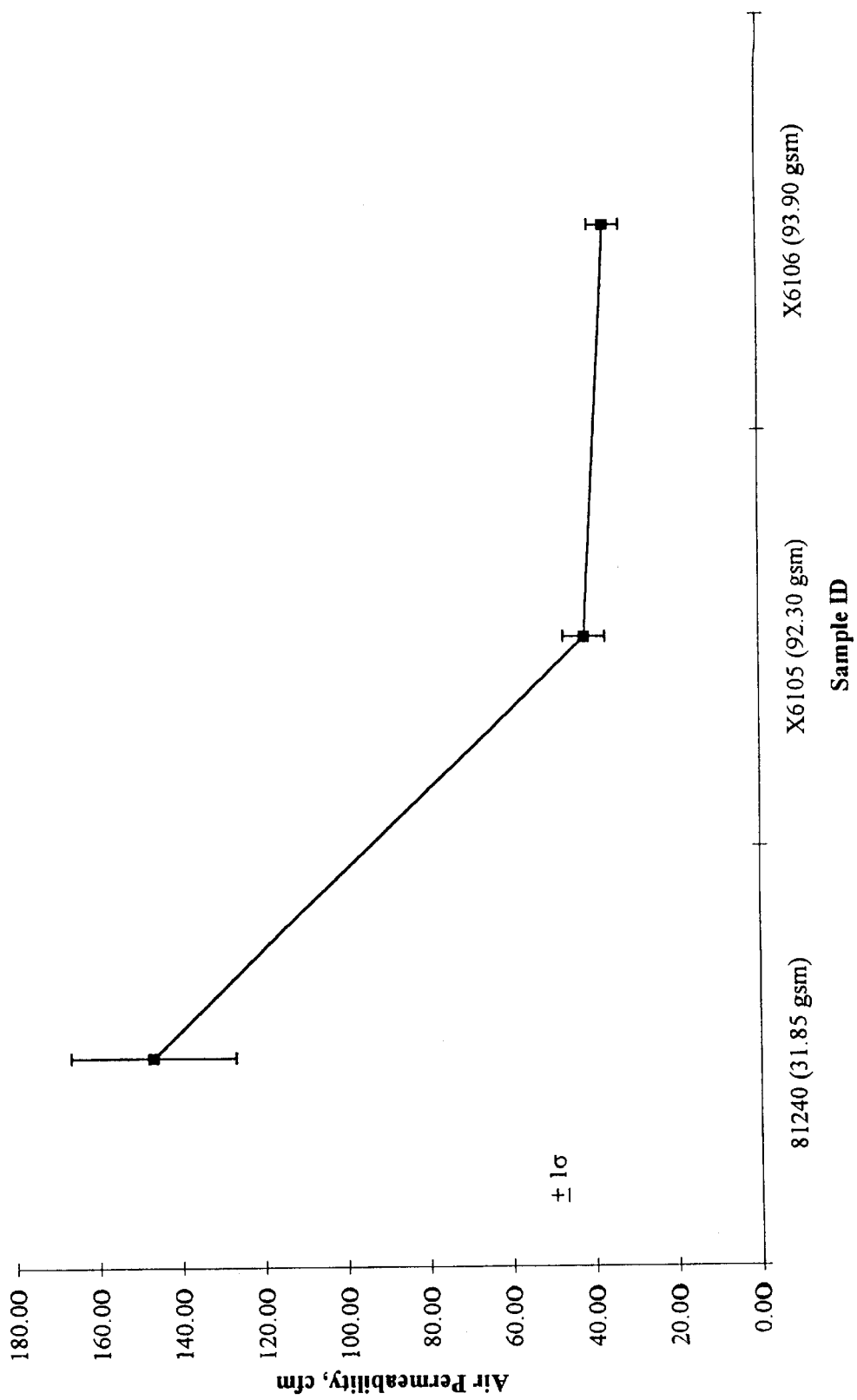

BREATHABLE DISPOSABLE SANITARY PRODUCT CONSTRUCTION AND BACKSHEET THEREFOR

CROSS-REFERENCE TO RELATED APPLICATION

This is a continuation-in-part of U.S. Patent application Ser. No. 08/720,631, filed Oct. 2, 1996, itself a continuation-in-part of U.S. Patent application Ser. No. 08/552,727, filed Nov. 3, 1995, now U.S. Pat. No. 5,643,239.

BACKGROUND OF THE INVENTION

The present invention relates to breathable diapers, feminine hygiene or like disposable sanitary product constructions, and more particularly to such a construction which is breathable and has an outer or backsheet surface which is cloth-like.

Disposable diapers for infants and incontinent older people are a major industry and, as such, constitute a crowded art, competitively speaking. In general, such sanitary product constructions comprise, from the skin-facing side outwardly, an inner topsheet (also called a cover or front sheet) which is liquid-permeable to facilitate entry of the fluid exudate from the wearer into the construction, a core of highly absorbent material for absorbing liquid received through the topsheet, and an outer backsheet formed of a vapor- and liquid-impermeable plastic to eliminate leakage of fluid from the diaper.

Such diapers have not proven to be entirely satisfactory. While the inner topsheet is typically in the form of a cloth-like material having a soft hand (which is correctly perceived as being comfortable for the baby to have adjacent to its skin), the outer backsheet plastic presents a rather cold, clammy surface which is at least perceived of as inhospitable and uncomfortable for the baby's skin. Further, the feel of the plastic backsheet to the parent or caregiver is inhospitable and uncomfortable in comparison to conventional cloth diapers. While the outer backsheet is less likely to come into contact with the baby's skin then the inner topsheet, the plastic backsheet is still perceived of as a negative and presumably discourages potential customers for disposable diapers in favor of cotton diapers.

Further, the plastic backsheet is impervious not only to liquid, but generally to heat and water vapor as well. Accordingly, the moisture vapor and the heat generated by the bodily exudate trapped within the diaper lead to conditions adjacent the wearer's skin which promote skin irritation, infection, and the like.

While the plastic backsheet is generally effective in precluding the passage of bodily exudate outwardly therethrough where the highly absorbent core is present, it is not efficient in preventing side leakage—that is, lateral leakage of liquids from the opposed side portions of the core sidewards between the leg gathers of the backsheet and the baby's skin. The obvious solution to the problem—tightening of the leg gathers—in turn presented problems in terms of the comfort of the baby, skin irritation, etc.

Accordingly, it is an object of the present invention to provide in one preferred embodiment a breathable diaper, feminine hygiene or like disposable sanitary product construction which has a cloth-like outer backsheet surface.

Another object is to provide in one preferred embodiment such a construction which is breathable to enable the escape of water vapor and heat therethrough.

A further object is to provide in one preferred embodiment such a construction which efficiently limits side leakage.

It is also an object of the present invention to provide a preferred embodiment of a disposable sanitary product construction having a backsheet surface which is cloth-like and of good hand, is breathable, and affords an efficient system for limiting side leakage.

It is a further object to provide such a construction which is simple and inexpensive to manufacture.

SUMMARY OF THE INVENTION

It has now been found that the above and related objects of the present invention are obtained in a breathable diaper, feminine hygiene or like disposable sanitary product construction having a cloth-like outer surface. The construction includes a plurality of materials comprising, from the skin-facing side outwardly, a topsheet, a core, an optional barrier and a backsheet. The topsheet is formed of liquid- and vapor-permeable hydrophilic material. The core is formed of highly absorbent material for absorbing fluid received through the topsheet. The core has an inner surface in fluid communication with the topsheet, an outer surface and two lateral side surfaces. The optional barrier is formed of a multilayer non-woven material which is hydrophobic and vapor permeable for limiting the outward escape of liquid therethrough while enabling the outward escape of heat and water vapor therethrough. The barrier has a base disposed adjacent the core outer surface. The backsheet is formed of a multilayer non-woven material which is hydrophobic and vapor permeable for limiting the outward escape of liquid therethrough while enabling the outward escape of heat and water vapor therethrough. The backsheet is disposed at least partially outwardly of the barrier base and as the outer surface of the construction.

In a preferred embodiment, the backsheet and/or barrier material is SM, a two-layer spunbond-meltblown non-woven fabric formed of a spunbond layer and a meltblown layer. In an optimal embodiment, the backsheet and/or barrier material is SMS, a three-layer spunbond-meltblown-spunbond non-woven fabric formed of two spunbond layers and a meltblown layer disposed intermediate the spunbond layers and bonding them together. The construction may include an additive or coating which increases the hydrophobicity of the material. The liquid contact angle of the non-woven fabric can be suitably adjusted to improve the hydrohead.

The topsheet may be a one-layer spunbond non-woven material, a liquid-distributing material, or a two-layer fabric formed of an inner layer of a liquid and vapor-permeable hydrophilic non-woven material and an outer layer of a liquid-distributing material. Preferably the barrier base is thicker than the barrier flanges to further limit the outward escape of liquid therethrough. A portion of the backsheet material may include elastic material such that, in use, a portion of the backsheet material is gathered about the legs of the user.

The construction preferably includes a hydrophobic enhancer formed of a multilayer non-woven material which is hydrophobic and vapor-permeable for limiting the outward escape of liquid therethrough while enabling the outward escape of heat and water vapor therethrough. The hydrophobic enhancer is disposed at least partially outwardly of the barrier base and inwardly of the backsheet. The hydrophobic enhancer is preferably SM or SMS. The hydrophobic enhancer may be a hydrophobic coating disposed adjacent an inner surface of the backsheet, the coating being polymeric, but cracked or fractured to provide breathability thereto. The cracked coating is preferably an ethyl vinyl acetate (EVA) extrusion having cracks or fractures sufficient to provide breathability thereto.

The present invention further encompasses a new backsheet for a breathable diaper, feminine hygiene, or like disposable sanitary product construction (whether or not it includes a barrier), which backsheet limits the outward escape of liquid therethrough while enabling the outward escape of heat and water vapor therethrough. The backsheet is adapted to be disposed at least partially as an outer layer of the construction, and has a front layer, a back layer and liquid-absorbent particles. The front layer is selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate the spunbond layers and bonding them together. The back layer is selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate the spunbond layers and bonding them together. The liquid-absorbent particles are disposed intermediate the front and back layers.

In a preferred embodiment the backsheet additionally including a binder for the particles and for binding the front and back layers of the backsheet together. Preferably, the binder is ethyl vinyl acetate or polyethylene, and the absorbent powder: binder powder ratio is 60:40 to 70:30% by weight. Preferably, each of the front and back layers has a 21–31 basis weight (gsm), and the particles have a 28–34 basis weight (gsm). Each of the front and back layers preferably consists of a three-layer spunbond-meltblown-spunbond non-woven fabric. The non-woven fabric of the backsheet is hydrophobic and vapor permeable. The front and back layers of the backsheet define a pouch containing the particles. The pouch is initially hydrophobic, but, when subjected to a sufficiently high hydrohead, becomes hydrophilic.

Finally, the present invention also encompasses a disposable sanitary product construction using such a new backsheet as the outer layer, preferably in the absence of a barrier sheet.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein:

FIG. 12 is a graph showing the hydrohead column (i.e., the hydrostatic head) as a function of air permeability for the substrate 81236 and the two backsheet samples X6102 & X6107;

FIG. 13 is a graph similar to FIG. 12 for the substrate 81238 and the two backsheet samples X6101 & 6104;

FIG. 14 is a graph similar to FIG. 12 for the substrate 81240 and the two backsheet samples X6105 & X6106;

FIG. 15 is a graph showing the slow strip tensile data (MD) for the materials of FIG. 12;

FIG. 16 is a graph showing the slow strip tensile data (CD) for the materials of FIG. 12;

FIG. 17 is a graph showing the rising water data for the materials of FIG. 12;

FIG. 18 is a graph showing the air permeability data for the materials of FIG. 12;

FIG. 19 is a graph showing the slow strip tensile data (MD) for the materials of FIG. 13;

FIG. 20 is a graph showing the slow strip tensile data (CD) for the materials of FIG. 13;

FIG. 21 is a graph showing the rising water data for the materials of FIG. 13;

FIG. 23 is a graph showing the slow strip tensile data (MD) for the materials of FIG. 14;

FIG. 24 is a graph showing the slow strip tensile data (CD) for the materials of FIG. 14;

FIG. 25 is a graph showing the rising water data for the materials of FIG. 14;

FIG. 26 is a graph showing the air permeability data for the materials of FIG. 14;

DETAILED DESCRIPTION OF THE PREFERRED EMBODIMENTS

Figure 1:
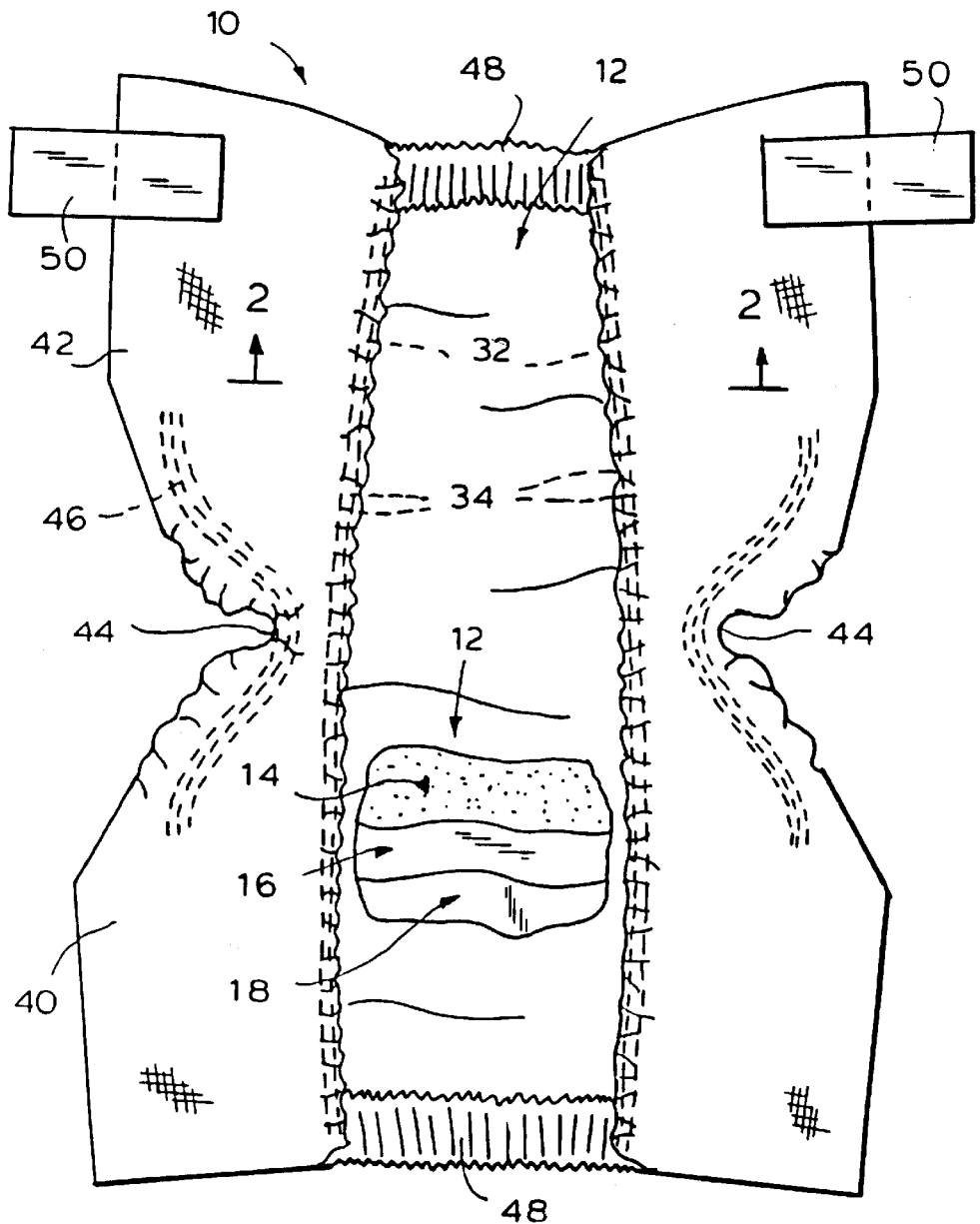
FIG. 1 is a top plan view of a simple embodiment of a diaper according to the present invention, with successive portions thereof being removed to reveal details of internal construction.
Figure 2:
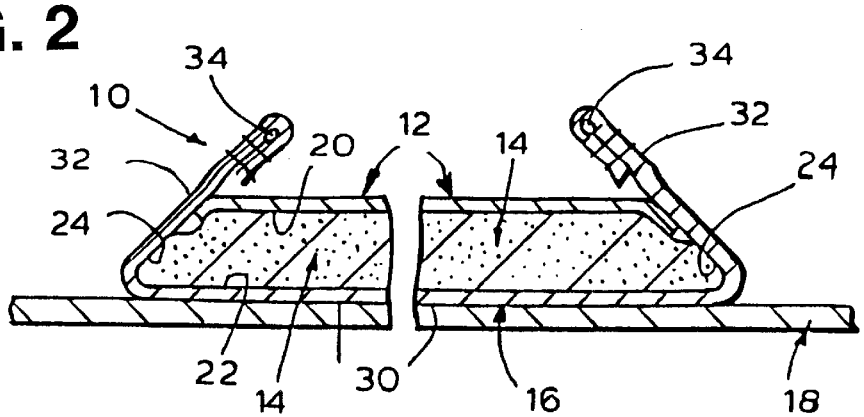
FIG. 2 is a sectional view thereof taken along the line 2—2 of FIG. 1.

Referring now to the drawing, and in particular to FIGS. 1 and 2 thereof, therein illustrated is a simple embodiment of a breathable diaper according to the present invention, generally designated by the reference numeral 10. As will be appreciated by those skilled in the art, the principles of the disposable sanitary product construction may be used for other disposable sanitary products such as feminine hygiene products, e.g., catamenial pads and the like, although typically the manner of securing the construction in place on the wearer's body will differ.

The construction 10 includes a plurality of materials comprising, from the skin-facing side outwardly, a topsheet generally designated 12, a core generally designated 14, a barrier generally designated 16, and a backsheet generally designated 18.

As is typical in these constructions, the topsheet 12 is formed of a liquid- and vapor-permeable hydrophilic material. For example, a preferred topsheet is formed of a one-layer, spunbond, non-woven fabric, with a soft, cloth-like surface for contact with the wearer's skin. While various liquid- and vapor-permeable hydrophilic materials may be used for the topsheet 12, a satisfactory diaper must be capable of providing the cloth-like inner surface affording good hand (e.g., softness).

Alternatively, the topsheet 12 may be formed of a liquid-distributing material, preferably one offering the same soft cloth-like feel as the spunbond topsheet. The liquid-distributing material performs a wicking service, drawing the liquid of the exudate away from the wearer and spreading it over a greater area of the topsheet 12 for transmission to the core 14.

Figure 3:
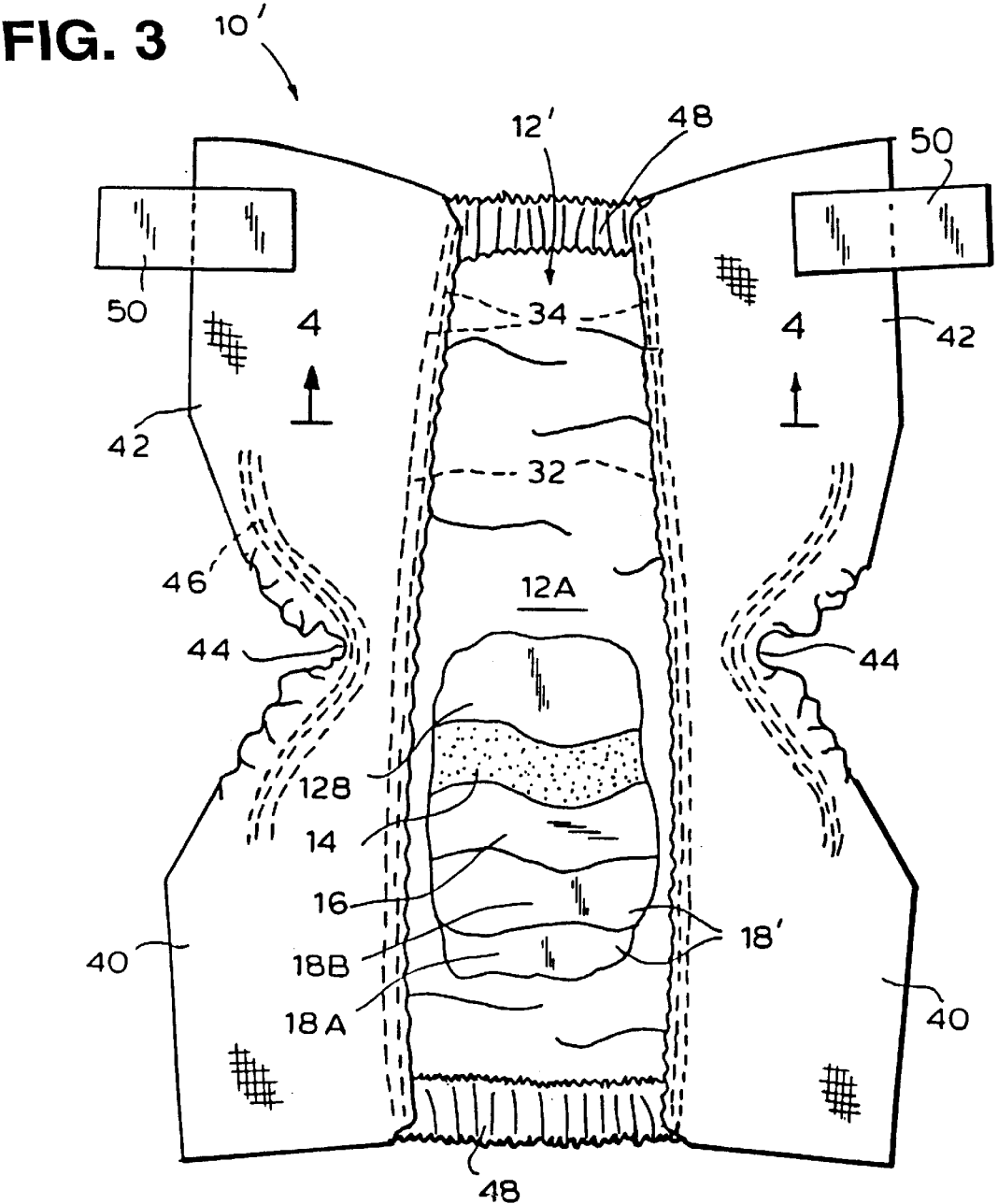
FIG. 3 is a top plan view of a more complex embodiment with successive portions thereof being removed to reveal details of internal construction.
Figure 4:
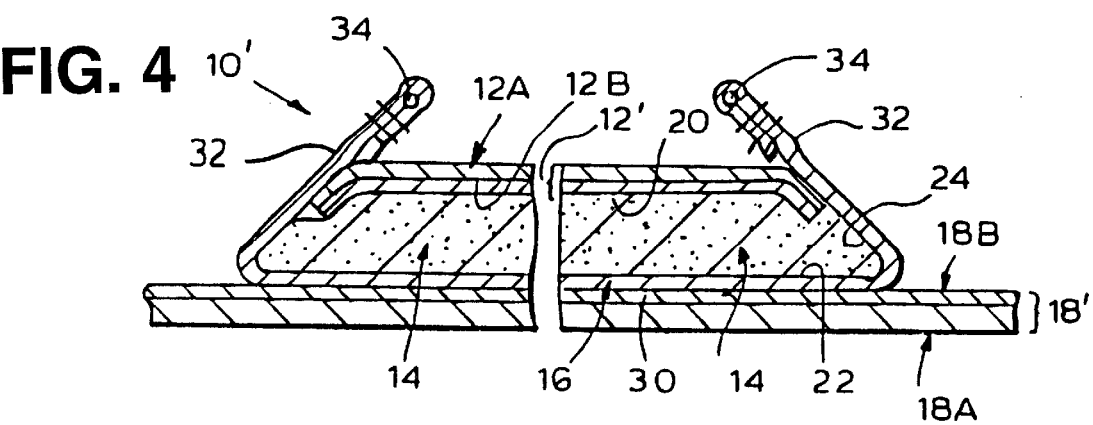
FIG. 4 is a sectional view thereof taken along the line 4—4 of FIG. 3.

In the preferred, more complex embodiment 10' of the diaper illustrated in FIGS. 3 and 4, the topsheet 12' is a two-layer fabric formed of an inner layer 12A of a liquid- and vapor-permeable, hydrophilic, non-woven material, and an outer layer 12B formed of a liquid-distributing material. Thus the preferred topsheet 12' is not only a liquid- and vapor-permeable hydrophilic material, but also a fluid-distributing material.

The topsheet 12 may comprise any of the materials heretofore employed for topsheets, e.g., spunbonded, polyester or polypropylene fibers, various non-woven fabrics, etc. having the desired wet and dry strengths as well as the liquid and vapor-permeability and hydrophilic characteristics earlier mentioned.

Referring now to FIGS. 1–4, in both embodiments 10 and 10', the core 14 is formed of a highly absorbent material and is disposed outwardly of the topsheet 12, 12' for absorbing liquid received through the topsheet. The core 14 has an inner surface 20 in liquid communication with the topsheet, an outer surface 22, and two lateral side surfaces 24, 24. (Typically, the core 14 extends longitudinally along the crotch, with the lateral side surfaces thereof being generally parallel to that longitudinal axis.) The core may be composed of any of the absorbent materials heretofore employed for that purpose in the diaper art, e.g., wood pulp or fluff, absorbent cotton fibers, polyester or polypropylene and the like, including mixtures thereof. Preferably, the core 14 is formed of a superabsorbent or like material which wicks the liquid received from the topsheet through and away from the topsheet, so that the topsheet generally presents a relatively dry inner surface to the wearer. As highly absorbent materials suitable for the core are well known in the conventional diaper, feminine hygiene and like sanitary product constructions art, further details thereof need not be provided herein.

The barrier 16 is disposed partially outwardly of the core 14 and is formed of a multilayer, non-woven material which is hydrophobic and vapor-permeable for limiting the outward escape of liquid therethrough, while enabling the outward escape of heat and water vapor therethrough. It has been found that the heat and humidity released by the accumulated body exudates, such as urine and feces, promote the irritation and itching which frequently develops when conventional disposable diapers are used. The barrier 16 of the present invention enables the heat and water vapor to escape outwardly from the core 14, through the barrier 16 and then further outwardly while at the same time limiting the outward escape of liquid (e.g., urine, blood, etc.) therethrough. The non-woven material may be spunbond, carded, spun-laced, meltblown or the like. A chemical finish may be applied in order to enhance its ability to repel specific liquids. The preferred materials are polyethylene, polypropylene, and the like.

Figure 5:
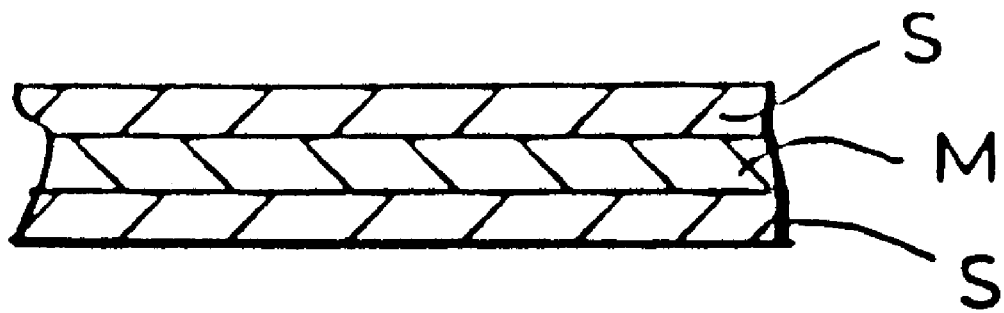
FIG. 5 is a fragmentary sectional view of a multilayered non-woven material—namely, a spunbond-meltblown-spunbond material.

The barrier material 16 is preferably SM or optimally SMS. SM is a two-layer spunbond-meltblown non-woven fabric formed of a spunbond layer and a meltblown layer. When SM is used, the meltblown layer is typically the inner layer. Referring now to FIG. 5, SMS is a three-layer, spunbond-meltblown-spunbond non-woven fabric formed of two spunbond layers S and a meltblown layer M disposed intermediate the spunbond layers and bonding them together. The spunbond and meltblown layers are typically formed of the same composition—preferably either polyethylene or propylene—although different compositions formed of other natural or synthetic materials may be used. Typically, the meltblown material is similar to the spunbond material, both fibers being essentially continuous, except that the fiber diameters are substantially smaller (such that the meltblown material by itself lacks tenacity and cannot be used by itself). Multilayer non-woven materials which are hydrophobic and vapor-permeable (i.e., water vapor-permeable) are well known in the art, and accordingly it is not deemed necessary to set forth herein further details thereof. It will be appreciated, however, that the layers forming the SM or SMS material may contain conventional additives to increase the hydrophobicity of the material, or even a coating, so long as the aforementioned desirable properties of the material are that adversely affected.

When the diaper is in use, as illustrated in FIG. 2, barrier 16 is U-shaped in cross section and has a base 30 at least partially disposed adjacent the outer surface 22 of the core 14 and a pair of flanges 32 upstanding from the base 30. Each of the flanges 22 extends inwardly (towards the topsheet 12) closely adjacent to a respective one of the core lateral side surfaces 24.

Even after distribution over the major face of the core 14 by a liquid-distributing topsheet 12, 12', the liquid passing from the core 14 to the barrier 16 still tends to bunch at the center of the core 14 rather than at the lateral sides 24 thereof. Accordingly, preferably the barrier base 30 is thicker than the barrier flanges 32, thereby to further limit the outward escape of liquid through the barrier base 30.

A portion of the barrier flanges 32, especially adjacent the free ends thereof, includes elastic or other biasing material 34 such that, when worn, a portion of the barrier flanges 32 are gathered about the legs of the user, thereby to prevent the escape of liquid laterally from the diaper. The elastic material 34 may be embedded in a folded-over free end of the barrier flanges 32, as illustrated, or it may simply be glued or stitched thereto. Thus, when the diaper 10 or 10' is tautly stretched out, as illustrated in FIGS. 1 and 3, the barrier flanges 32 lay flat over the topsheet 12 or 12' and core 14 while, when the diaper is worn as illustrated in FIGS. 2 and 4, the barrier flanges 32 stand upright to prevent the lateral escape of liquid exudate from the diaper. Optionally the free ends of the barrier flanges 32 may be secured to the lateral edges of the top sheet 12 to limit liquid leakage therebetween.

It will be appreciated that the core 14 is encapsulated on all four sides: by the topsheet 12, 12' on its inner surface 20, the barrier base 30 on its outer surface 22, and the barrier flanges 32 on its lateral sides 24.

The backsheet 18, like the barrier 16, is formed of a multilayer non-woven material which is hydrophobic and vapor-permeable for limiting the outward escape of liquid therethrough while enabling the escape of heat and water vapor therethrough. The preferred backsheet material is a two-layer SM or a three-layer SMS, as described above. The backsheet 18 is at least partially disposed outwardly of the barrier base 30. Any liquid which passes out of the core 14 and through the barrier 16 encounters the backsheet 18, which further limits its outward escape.

The backsheet 18 is typically formed in the configuration of a conventional diaper having a front portion 40, a rear portion 42 and a crotch portion 44 therebetween. The crotch portion 44 typically includes elastic threads 46 for gathering the backsheet 18 around the legs of the wearer. The central longitudinal portion of the backsheet 18 may define gathers 48 at its opposed waist ends to assist in shaping the diaper and keeping the various components thereof in place—for example, by stitching therethrough to drape the gathers 48.

Conventional mechanical fasteners 50, such as adhesive or VELCRO (trademark of VELCRO USA Inc.) tabs, are permanently fastened to the rear portion 42 of backsheet 18 so that they may be releasably attached to the front portion 40 when the diaper is placed on the wearer. The pair of conventional fasteners in the waist area permit releasably securing or refastening of the opposed ends of the backsheet 18 together around the waist of the wearer where the diaper is folded to engage the front and back of the body. The fasteners may employ refastenable pressure-sensitive adhesive and may be elastic in nature.

The presence of a backsheet 18 formed of a multilayer, non-woven material enables the outer surface of the diaper to have an outer surface with a cloth-like feel similar to that of a conventional cloth diaper. Accordingly, a potential purchaser of the diaper will be under the impression that he/she is affording twice the comfort and protection of a conventional diaper because a soft, cloth-like material forms both the topsheet 12 and the backsheet 18.

In the preferred, albeit more complex, embodiment 10' of the present invention illustrated in FIGS. 3 and 4, the construction 10' includes the backsheet 18' defining diaper outer surface 18A and a hydrophobic enhancer 18B formed of a multilayer, non-woven material. The multilayer, non-woven material of enhancer 18B is hydrophobic and vapor-permeable for limiting the outward escape of liquid therethrough while enabling the outward escape of heat and water vapor therethrough. The preferred enhancer material is a two-layer SM or a three-layer SMS as described above.

Preferably the hydrophobic enhancer 18B is at least partially disposed outwardly of the barrier base 30 and inwardly of the backsheet 18A. Indeed, the hydrophobic enhancer 18B may simply be a coating disposed adjacent the inner surface of backsheet 18A. The hydrophobic coating is preferably cracked or fractured to provide breathability thereto. Preferred coatings are polymers—e.g., an ethyl vinyl acetate (EVA) extrusion having cracks or fractures sufficient to provide breathability therethrough. It will be appreciated that the presence of the enhancer 18B as either a separate layer or as a coating on the inner surface of backsheet 18A does not detract from the desirable soft feel of the latter.

Liquid exudate escaping from the lateral sides of the core 14 are initially blocked by the barrier 16 and trapped in the U-shaped well 32, 30, 32 of the barrier 16. Even if the liquid exudate escapes the well of the barrier, it is still retained within the diaper by the backsheet 18 or the hydrophobic enhancer 18B and backsheet 18A, depending upon the embodiment of the diaper.

The various materials 12, 14, 16, 18 of diaper 10 or 12A, 12B, 14, 16, 18A, 18B of diaper 10' may be secured together with hot-melt or like adhesives or even simple mechanical or stitching means, as is customary in the diaper art.

The diaper 10, 10' according to the present invention is used in the same manner as a conventional diaper.

Figure 6:
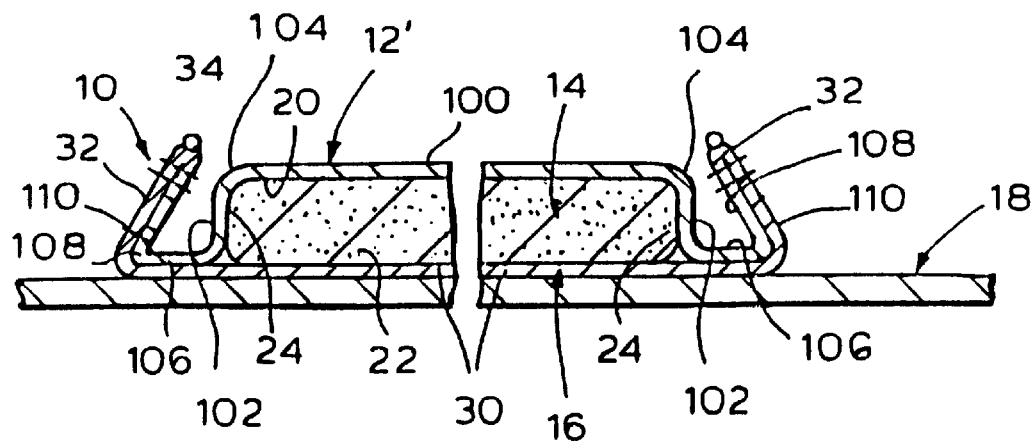
FIG. 6 is a sectional view of a variant of the simple embodiment.
Figure 7:
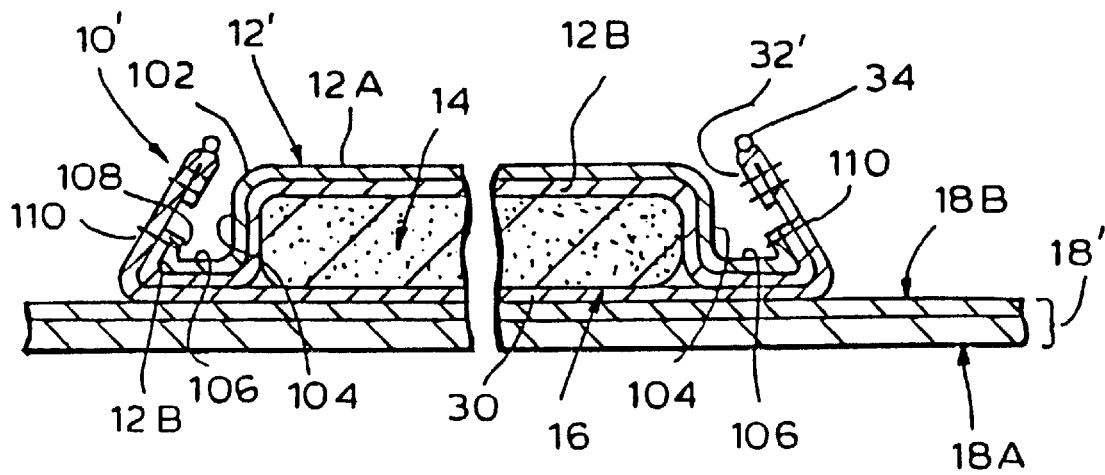
FIG. 7 is a sectional view of a variant of the more complex embodiment.

While the embodiments illustrated in FIGS. 1–4 have the barrier flanges 32 disposed contiguous to the core lateral side surfaces 24, and only optionally secured to the topsheet 12, alternatively the topsheet 12 and the barrier 16 may be directly secured together at a location optionally spaced from core 14. Thus, as illustrated in FIG. 6, the topsheet 12' defines a topsheet base 100 disposed adjacent the core inner surface 20 and a pair of topsheet flanges 102 extending outwardly from the topsheet base 100. The topsheet flanges 102 are U-shaped, each topsheet flange 102 having one leg 104 disposed contiguous to or very closely adjacent to the core lateral side surface 24, the topsheet base 106 being disposed generally parallel to the barrier base 30, and the other topsheet flange leg 108 being secured to the barrier flange 32, as illustrated at 110. As illustrated in FIG. 7, clearly the principles of this variant are equally applicable to a variant of the more complex embodiment illustrated in FIGS. 3 and 4, and, indeed, the configuration of the topsheet flanges and the barrier flanges may be varied substantially as long as each topsheet flange is secured to a respective barrier flange in such a manner as to minimize side leakage.

To summarize, the present invention provides a breathable diaper, feminine hygiene or like disposable sanitary product construction which has a cloth-like outerback sheet surface, is breathable to enable the escape of water vapor and heat therethrough, and efficiently limits side leakage of liquid. The construction is simple and inexpensive to manufacture.

Notwithstanding the foregoing, it has been found that the invention described above can be improved to further preclude the possibility of leakage in the event that the bodily exudate flow is substantial (e.g., in overnight use). This is done without sacrificing the backsheet being vapor-permeable, thereby to enable the outward escape of heat and water vapor therethrough, and without sacrificing the outer backsheet surface being cloth-like.

More particularly, the new backsheet according to the present invention, generally designated 300, is disposed at least partially as an outer layer of a disposable sanitary product construction. It includes a front layer 302, a back layer 304, and liquid-absorbent particles 310 disposed intermediate the front and back layers 302, 304. The front layer 302 and the back layer 304 are preferably hydrophobic and vapor-permeable, each being independently selected from the group consisting of (a) an at least two-layer spunbond-meltblown or SM non-woven fabric (formed of a spunbond layer and a meltblown layer), as illustrated in FIG. 8, and (b) an at least three-layer spunbond-meltblown-spunbond or SMS non-woven fabric (formed of two spunbond layers and a meltblown layer disposed intermediate the spunbond layers and bonding them together), as illustrated in FIG. 9.

In a two-layer spunbond-meltblown or SM non-woven fabric, the meltblown layer M is typically on the inner or skin-facing side of the spunbond layer S. While the spunbond layer S and the meltblown layer M are preferably formed of polypropylene, different compositions of natural or synthetic materials may be used. Preferably, the spunbond layers of the substrate were made from Exxon 3445, and the meltblown layers of the substrate were made from Montell 3495G resin.

Figure 8:
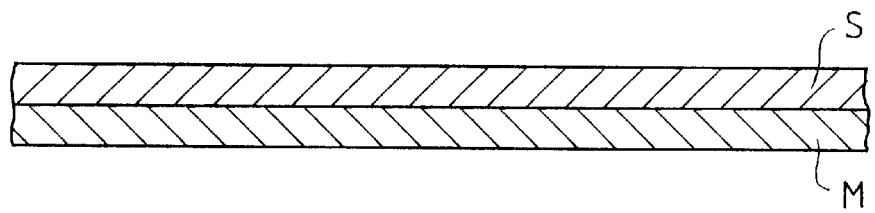
FIG. 8 is a fragmentary sectional view of an SM substrate sheet.
Figure 9:
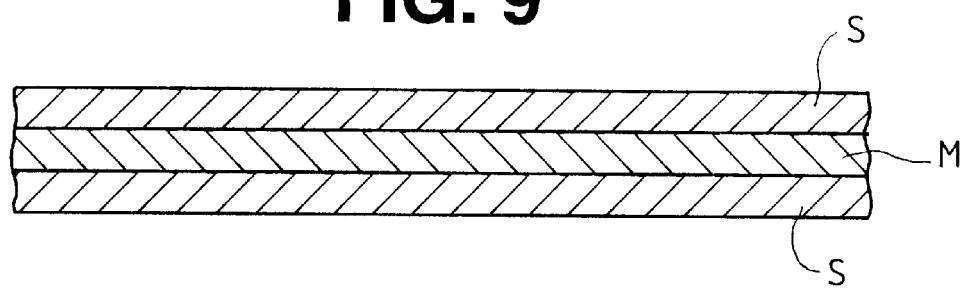
FIG. 9 is a fragmentary sectional view of an SMS substrate sheet.

While the front layer 302 and the back layer 304 are preferably each independently selected from the group consisting of (a) a two-layer SM non-woven fabric, as illustrated in FIG. 8, and (b) a three-layer SMS non-woven fabric, as illustrated in FIG. 9, the two-layer SM and the three-layer SMS may include additional layers (e.g., additional M layers) not substantially adversely affecting the desired properties of the fabric such as vapor permeability and hydrohead. Preferably in the back layer 304, the outer surface is formed by a spunbond S layer in order to provide the cloth-like outer backsheet surface feature.

It will be appreciated that the new backsheet 300 is employed as the backsheet 18 of the simple or more complex embodiments described above (regardless of whether the front layer 302 and the back layer 304 are of the at least two- or at least three-layer non-woven fabrics). No barrier sheet is required with the new backsheet 300, although optionally one may be used. Preferably each of the front and back layers 302, 304 consists of a three-layer SMS non-woven fabric. Each of the front and back layers 302, 304 preferably has a 21–31 basis weight (GSM), while the particles 310 have a 28–34 basis weight (GSM).

Figure 10:
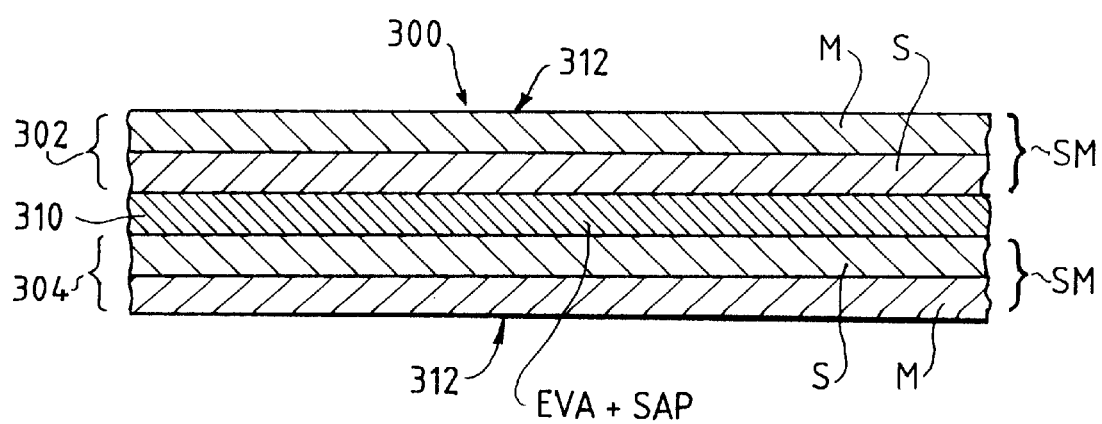
FIG. 10 is a sectional view of the new SM/SM backsheet (without binder) according to the present invention.
Figure 11:
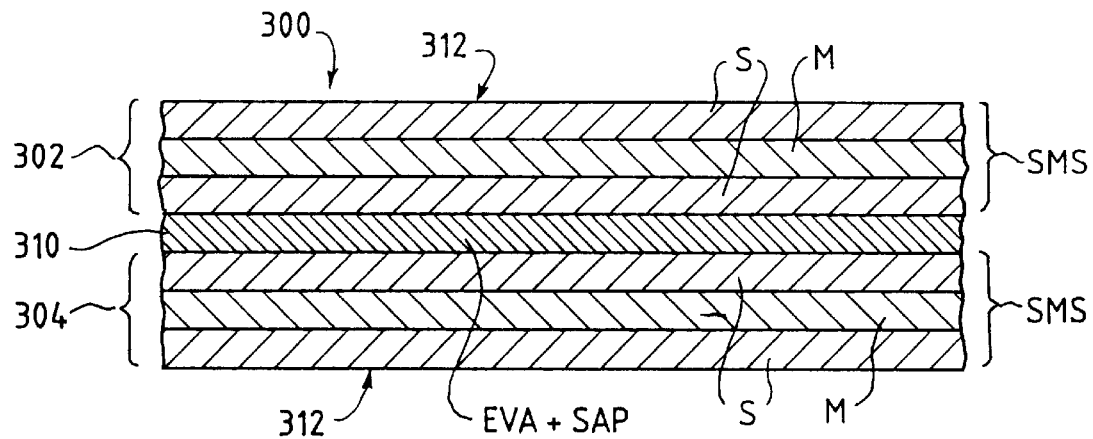
FIG. 11 is a view similar to FIG. 10 but of the new SMS/SMS backsheet (without binder) according to the present invention.

Referring now to FIGS. 10–11, the front and back layers 302, 304 of the new backsheet 300 define a pouch, generally designated 312, which contains the particles 310. In FIG. 10 the layers are SM. In FIG. 11 the layers are SMS. The pouch 312 is initially hydrophobic but, when subjected to a sufficiently high hydrohead, becomes hydrophilic.

The absorbent particles 310 disposed in the pouch 312 formed by the front layer 302 and the back layer 304 are preferably superabsorbent—e.g., SAP (a sodium salt of an acrylic based copolymer), EVA (an ethyl vinyl acetate copolymer), or a combination thereof. If desired, ordinary absorbent particles (rather than superabsorbent particles) may be used.

Figure 11A:
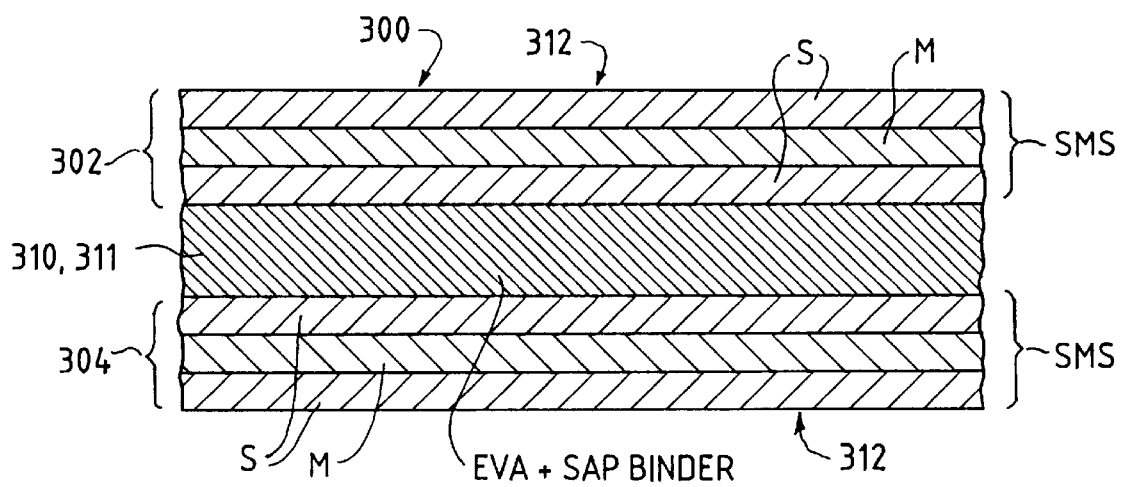
FIG. 11A is a view similar to FIG. 11, but with a binder.

As illustrated in FIG. 11A, a binder 311 may be used for binding the absorbent particles 310 together and/or for binding together the front and back layers 302, 304 of the barrier sheet 300. The preferred binder 311 is ethyl vinyl acetate or polyethylene. A preferred polymer powder binder powder ratio is 60:40 to 70:30 by weight.

The particle size distribution of the absorbent particles 310 is preferably maintained sufficiently low so as to not adversely affect the absorbency (or superabsorbency) of the particles. The particle size 5 distributions for the preferred particle materials are as follows:

SAP: particle size distribution of NORSOCRYL S35, a sodium salt of an acrylic based copolymer available from ELF ATOCHEM (Germany)—
>800 microns (0.8 mm): 0.14%
500<>800 microns: 1.2%
<100 microns: 2.78%
remaining quantities of the particles (95.88%) between 100 and 500 microns
bulk density 0.44 g/cc EVA: particle size distribution of PLATABOND M 1432 PA 600/35, an ethyl vinyl acetate copolymer available from ELF ATOCHEM (France)—
>200 microns: 23.0%
>400 microns: 86.6%
>600 microns: 99.4%
>800 microns: 0.0%
76.4% of the particles are between 200 and 600 microns
bulk density: 0.43 g/cc The powder form of absorbent particles 310 may be dispensed on one or both of the front and back layers 302, 304 using a scatter coating head (not shown) available from Villars (now a part of Cavitec of Switzerland). In this head, particle powder is distributed by a cylinder covered with a metallic clothing, like a card cylinder. Powder fills the gaps between the rows of the clothing and falls down on the material to be coated due to the rotation of the cylinder. The coating weight depends upon the rotational speed of the cylinder.

The pouch 312 then undergoes a process of web consolidation (such as calendering) to at least marginally secure together the front and back layers.

Preferably any such calendering occurs below the distortion temperature of the materials. In those instances where the front and back layers 302, 304 do not adhere together well, an adhesive add-on (not shown) may be employed between the two components—e.g., a layer of hot-melt adhesive applied to the outer margins of the layers of the pouch.

While a hydrohead of at least 15 centimeters in considered to be more than adequate, even for diaper applications, the new backsheet 300 typically has a greater hydrohead of 38–42 cms. While an air permeability of at least 10 cfm is considered desirable, the new backsheets 300 had a higher air permeability of 37–42 cfm. Accordingly, the new backsheet 300 represents an improvement over the backsheet 18 (and constructions made therewith represent improvements over the constructions made with the backsheet 18) because of the higher hydroheads (at least twice the 15 centimeters considered to be more than adequate) and the higher air permeability (at least four times the 10 CFM considered desirable).

EXAMPLE I

In order to illustrate the manufacture of the materials of the present invention and their efficacy, various samples were created by applying a powder blend between two substrates to create a new backsheet, and the new backsheet was tested.

The front and back sheets (that is, substrates 1 and 2) were both polypropylene. The same material was used for substrate 1 and substrate 2 in each trial.

There were three trials (X6107, X6101 and X6016) using different basis weight polypropylenes (29, 30 and 31 gsm, respectively) for the substrates, with a 60/40 SAP/EVA powder blend used in an amount of 34 grams per square meter. Similarly, there were three trials (X6102, X6104 and X6105) using different basis weight polypropylenes (29, 30 and 31 gsm, respectively) for the substrates with a 70/30 SAP/EVA powder blend used in an amount of 28 gsm.

In Table I, for each backsheet sample or trial, there is identified the weight of each component (in grams per square meter or gsm), the SAP/EVA ratio of the powder blend, and the total sample weight (in gsm). Table I additionally identifies for each trial the hydrostatic head (in millimeters of water column) and the peeling strength (in grams per 50 millimeters).

The hydrostatic head was measured by Poly-bond Inc.'s "rising water column" test wherein water rises at 254 mm per minute, gradually increasing the pressure to a suspended specimen. The test continues until water penetrates the specimen.

Table II provides, for each substrate material and for each sample or trial number, test averages for various properties such as slow strip tensile (on 1×7 inch strips) in the machine direction and in the cross direction, rising water (in centimeters) and air permeability (in CFM).

Figure 22:
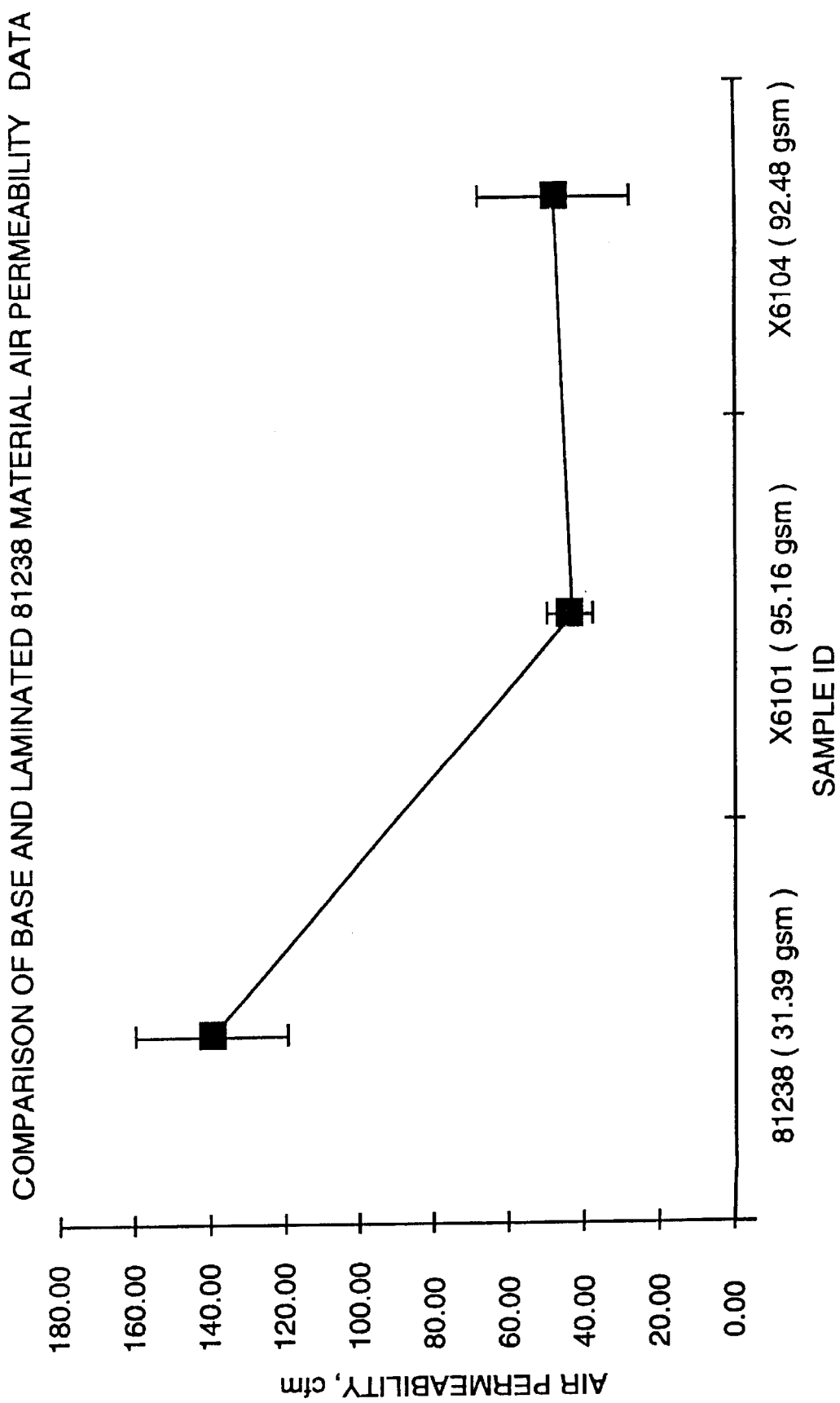
FIG. 22 is a graph showing the air permeability data for the materials of FIG. 13.

FIGS. 15 and 16, 19 and 20, 23 and 24 show the increase in slow strip tensile (both in the machine direction and the cross direction) when the new backsheet of the present invention is used in place of one of the substrates thereof. Similarly, FIGS. 17, 21 and 25 show the increase in the rising water test, while FIGS. 18, 22 and 26 show the decrease in air permeability (when the new backsheet of the present invention is compared to a single sheet of one substrate thereof).

The test results illustrate the relative merits of the new backsheet 300 vis-a-vis the various substrates for use in a breathable diaper, feminine hygiene or like disposable sanitary product construction which is breathable and has an outer or backsheet surface which is cloth-like. Each of the trial samples shows an acceptable air permeability and an acceptable hydrostatic head.

Now that the preferred embodiments of the present invention have been shown and described in detail, various modifications and improvements thereon will become readily apparent to those skilled in the art. Accordingly, the spirit and scope of the present invention is to be interpreted broadly and limited only by the appended claims, and not by the foregoing specification.

TABLE II

Backsheet Data Comparison

| Property | ID 81236 Average | X6102 Average | X6107 Average |
|---|---|---|---|
| Basis Weight, gsm | 31 | 94 | 100 |
| Air Permeability, cfm | 134 | 39 | 40 |
| Elongation - MD, % | 75 | 40 | 42 |
| Slow Strip Tensile - MD g/cm | 1246 | 2706 | 2481 |
| Tensile Energy Absorption - MD, cm* g/c | 742 | 1103 | 1038 |
| Load @ 5% Elongation - MD, g/cm | 314 | 1139 | 1009 |
| Elongation - CD, % | 76 | 42 | 53 |
| Slow Strip Tensile - CD, g/cm | 653 | 1023 | 1139 |
| Tensile Energy Absorption - CD, cm* g/c | 364 | 422 | 555 |
| Load @ 5% Elongation - CD, g/cm | 159 | 374 | 366 |
| Rising Water, cm | 22 | 37 | 36 |
| Peel Strength - MD, lbs |  | 0 | 0 |
| Peel Strength - CD, lbs |  | 0 | 0 |

| Property | ID 81238 Average | X6101 Average | X6104 Average |
|---|---|---|---|
| Basis Weight, gsm | 32 | 95 | 92 |
| Air Permeability, cfm | 141 | 41 | 42 |
| Elongation - MD, % | 83 | 49 | 36 |
| Slow Strip Tensile - MD g/cm | 1435 | 2722 | 2540 |
| Tensile Energy Absorption - MD, cm* g/c | 898 | 1214 | 919 |
| Load @ 5% Elongation - MD, g/cm | 428 | 1065 | 1041 |
| Elongation - CD, % | 71 | 48 | 45 |
| Slow Strip Tensile - CD, g/cm | 609 | 1084 | 1018 |
| Tensile Energy Absorption - CD, cm* g/c | 324 | 482 | 436 |
| Load @ 5% Elongation - CD, g/cm | 132 | 384 | 348 |
| Rising Water, cm | 22 | 38 | 39 |
| Peel Strength - MD, lbs |  | 0 | 0 |
| Peel Strength - CD, lbs |  | 0 | 0 |

| Property | ID 81240 Average | X6105 Average | X616 Average |
|---|---|---|---|
| Basis Weight, gsm | 32 | 92 | 94 |
| Air Permeability, cfm | 147 | 42 | 37 |
| Elongation - MD, % | 81 | 36 | 46 |

TABLE I

| Trial number | Substrate 1 Polybond style | Basis weight (gsm) | Substrate 2 Polybond style | Basis weight (gsm) | Powder blend SAP | EVA | Powder amount (gsm) Total | SAP | EVA | Total weight in gsm |
|---|---|---|---|---|---|---|---|---|---|---|
| X6107 | 81 236 | 29 | 81 236 | 29 | 60% | 40% | 34 | 20.4 | 13.6 | 92 |
| X6101 | 81 236 | 30 | 81 238 | 30 | 60% | 40% | 34 | 20.4 | 13.6 | 94 |
| X6106 | 81 240 | 31 | 81 240 | 31 | 60% | 40% | 34 | 20.4 | 13.6 | 96 |
| X6102 | 81 236 | 29 | 81 236 | 29 | 70% | 30% | 28 | 19.6 | 8.4 | 86 |
| X6104 | 81 238 | 30 | 81 238 | 30 | 70% | 30% | 28 | 19.6 | 8.4 | 88 |
| X6105 | 81 240 | 31 | 81 240 | 31 | 70% | 30% | 28 | 19.6 | 8.4 | 90 |

| Trial number | Hydrostatic head (in mm of water column) | | | | Peeling strength (in g/50 mm) | | | | Total weight gsm |
|---|---|---|---|---|---|---|---|---|---|
| | Left | Medium | Right | Average | Left | Medium | Right | Average | |
| X6107 | 440 | 380 | 400 | 407 | 60 | 40 | 40 | 47 | 101.43 |
| X6101 | 370 | 380 | 400 | 383 | 70 | 60 | 50 | 60 | 96.52 |
| X6106 | 440 | 380 | 430 | 417 | 60 | 40 | 50 | 50 | 98.40 |
| X6102 | 425 | 410 | 390 | 408 | 60 | 50 | 40 | 50 | 94.79 |
| X6104 | 385 | 385 | 380 | 383 | 60 | 50 | 80 | 63 | 92.67 |
| X6105 | 380 | 380 | 400 | 387 | 50 | 70 | 60 | 60 | 90.87 |

TABLE II-continued

Backsheet Data Comparison

| | | | |
|---|---|---|---|
| Slow Strip Tensile - MD g/cm | 1462 | 2356 | 2461 |
| Tensile Energy Absorption - MD, cm* g/c | 886 | 897 | 1142 |
| Load @ 5% Elongation - MD, g/cm | 439 | 1039 | 960 |
| Elongation - CD, % | 68 | 43 | 51 |
| Slow Strip Tensile - CD, g/cm | 610 | 943 | 1065 |
| Tensile Energy Absorption - CD, cm* g/c | 316 | 387 | 516 |
| Load @ 5% Elongation - CD, g/cm | 160 | 325 | 353 |
| Rising Water, cm | 19 | 38 | 38 |
| Peel Strength - MD, lbs | | 0 | 0 |
| Peel Strength - CD, lbs | | 0 | 0 |

We claim:

1. A disposable absorbent sanitary article including a plurality of materials comprising, from the skin-facing side outwardly:
   (A) a topsheet of liquid and vapor-permeable hydrophilic material;
   (B) a core of highly absorbent material disposed outwardly of said topsheet for absorbing liquid received through said topsheet, said core having an inner surface in liquid communication with said topsheet and an outer surface; and
   (C) a backsheet for limiting the outward escape of liquid therethrough while enabling the outward escape of heat and water vapor therethrough, said backsheet being disposed at least partially outwardly of said barrier base and formed from:
      (i) a front layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together;
      (ii) a back layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together; and
      (iii) liquid-absorbent particles disposed intermediate said front and back layers.

2. The article of claim 1 wherein additionally including a binder for said particles and for binding said front and back layers of said backsheet together.

3. The article of claim 2 wherein said binder is ethyl vinyl acetate or polyethylene.

4. The construction of claim 2 wherein the absorbent powder: binder powder ratio is 60:40 to 70:30% by weight.

5. The article of claim 1 wherein each of said front and back layers has a 21–31 basis weight (gsm), and said particles have a 28–34 basis weight (gsm).

6. The article of claim 1 wherein each of said front and back layers consists of a three-layer spunbond-meltblown-spunbond non-woven fabric.

7. The article of claim 1 wherein said non-woven fabric of said backsheet is hydrophobic and vapor permeable.

8. The article of claim 1 wherein said front and back layers of said backsheet define a pouch containing said particles.

9. The article of claim 8 wherein said pouch is initially hydrophobic but, when subjected to a sufficiently high hydrohead, becomes hydrophilic.

10. A disposable absorbent sanitary article including a plurality of materials comprising, from the skin-facing side outwardly:
    (A) a topsheet of liquid and vapor-permeable hydrophilic material;
    (B) a core of highly absorbent material disposed outwardly of said topsheet for absorbing liquid received through said topsheet, said core having an inner surface in liquid communication with said topsheet and an outer surface; and
    (C) a backsheet for limiting the outward escape of liquid therethrough while enabling the outward escape of heat and water vapor therethrough, said backsheet being disposed at least partially as an outer surface of the construction and formed from:
       (i) a hydrophobic and vapor permeable front layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together;
       (ii) a hydrophobic and vapor permeable back layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together;
       (iii) liquid-absorbent particles disposed intermediate said front and back layers, said front and back layers of said backsheet define a pouch containing said particles; and
       (iv) a binder for said particles and for binding said front and back layers of said backsheet together, said binder being ethyl vinyl acetate or polyethylene.

11. The article of claim 10 wherein each of said front and back layers consists of a three-layer spunbond-meltblown-spunbond non-woven fabric.

12. The article of claim 10 wherein each of said front and back layers has a 21–31 basis weight (gsm), and said particles have a 28–34 basis weight (gsm).

13. The article of claim 10 wherein the absorbent powder: binder powder ratio is 60:40 to 70:30% by weight.

14. A backsheet for a disposable absorbent sanitary article comprising:
    a backsheet for limiting the outward escape of liquid therethrough while enabling the outward escape of heat and water vapor therethrough, said backsheet being adapted to be disposed at least partially as an outer layer of the construction:
       (i) a front layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together;
       (ii) a back layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together; and (iii) liquid-absorbent particles disposed intermediate said front and back layers.

15. The backsheet of claim 14 additionally including a binder for said particles and for binding said front and back layers of said backsheet together.

16. The backsheet of claim 15 wherein said binder is ethyl vinyl acetate or polyethylene.

17. The backsheet of claim 15 wherein the absorbent powder: binder powder ratio is 60:40 to 70:30% by weight.

18. The backsheet of claim 14 wherein each of said front and back layers has a 21–31 basis weight (gsm), and said particles have a 28–34 basis weight (gsm).

19. The backsheet of claim 14 wherein each of said front and back layers consists of a three-layer spunbond-meltblown-spunbond non-woven fabric.

20. The backsheet of claim 14 wherein said non-woven fabric of said backsheet is hydrophobic and vapor permeable.

21. The backsheet of claim 14 wherein said front and back layers of said backsheet define a pouch containing said particles.

22. The backsheet of claim 21 wherein said pouch is initially hydrophobic but, when subjected to a sufficiently high hydrohead, becomes hydrophilic.

23. A backsheet for a disposable absorbent sanitary article comprising:

a backsheet for limiting the outward escape of liquid therethrough while enabling the outward escape of heat and water vapor therethrough, said backsheet being adapted to be disposed at least partially as an outer layer of the construction and formed from:

(i) a hydrophobic and vapor permeable front layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together;

(ii) a hydrophobic and vapor permeable back layer selected from the group consisting of (a) an at least two-layer spunbond-meltblown non-woven fabric formed of a spunbond layer and a meltblown layer and (b) an at least three-layer spunbond-meltblown-spunbond non-woven fabric formed of two spunbond layers and a meltblown layer disposed intermediate said spunbond layers and bonding them together;

(iii) liquid-absorbent particles disposed intermediate said front and back layers, said front and back layers of said backsheet define a pouch containing said particles; and (iv) a binder for said particles and for binding said front and back layers of said backsheet together, said binder being ethyl vinyl acetate or polyethylene.

24. The backsheet of claim 23 wherein each of said front and back layers consists of a three-layer spunbond-meltblown-spunbond non-woven fabric.

25. The backsheet of claim 23 wherein each of said front and back layers has a 21–31 basis weight (gsm), and said particles have a 28–34 basis weight (gsm).

26. The backsheet of claim 23 wherein the absorbent powder: binder powder ratio is 60:40 to 70:30% by weight.

* * * * *

UNITED STATES PATENT AND TRADEMARK OFFICE
CERTIFICATE OF CORRECTION

PATENT NO. : 5,928,209
DATED : July 27, 1999
INVENTOR(S) : Carl Allen Bodford, Roe Clyde Allen & Rahul Krishnakant Nayak It is certified that error appears in the above-identified patent and that said Letters Patent is hereby corrected as shown below:

Column 13, line 52, "construction" should be -- article --.

Signed and Sealed this

Fifteenth Day of August, 2000

Attest:

Q. TODD DICKINSON

Attesting Officer

Director of Patents and Trademarks